(12) United States Patent
Thakkar et al.

(10) Patent No.: US 12,029,903 B2
(45) Date of Patent: Jul. 9, 2024

(54) SYSTEMS AND METHODS FOR STRENGTHENING A RESPIRATORY MUSCLE

(71) Applicant: Lungpacer Medical Inc., Vancouver (CA)

(72) Inventors: Viral S. Thakkar, Chester Springs, PA (US); Douglas G. Evans, Downingtown, PA (US)

(73) Assignee: Lungpacer Medical Inc., Vancouver (CA)

(*) Notice: Subject to any disclaimer, the term of this patent is extended or adjusted under 35 U.S.C. 154(b) by 293 days.

(21) Appl. No.: 17/474,646

(22) Filed: Sep. 14, 2021

(65) Prior Publication Data
US 2022/0134095 A1 May 5, 2022

Related U.S. Application Data

(63) Continuation of application No. 15/837,519, filed on Dec. 11, 2017, now abandoned.

(51) Int. Cl.
*A61N 1/36* (2006.01)
*A61B 5/00* (2006.01)
(Continued)

(52) U.S. Cl.
CPC .......... *A61N 1/3601* (2013.01); *A61B 5/4519* (2013.01); *A61B 5/4836* (2013.01);
(Continued)

(58) Field of Classification Search
CPC .. A61N 1/3601; A61N 1/0551; A61N 1/0558; A61N 1/3611
See application file for complete search history.

(56) References Cited

U.S. PATENT DOCUMENTS

| | | | |
|---|---|---|---|
| 1,693,734 | A | 12/1928 | Waggoner |
| 2,532,788 | A | 12/1950 | Sarnoff |

(Continued)

FOREIGN PATENT DOCUMENTS

| | | | |
|---|---|---|---|
| CN | 1652839 A | | 8/2005 |
| CN | 102143781 A | | 8/2011 |

(Continued)

OTHER PUBLICATIONS

Reynolds, S.C. et al., "Mitigation of Ventilator-induced Diaphragm Atrophy by Transvenous Phrenic Nerve Stimulation," American Journal of Respiratory and Critical Care Medicine, vol. 195, pp. 339-348 (2017).

(Continued)

*Primary Examiner* — Brian T Gedeon
(74) *Attorney, Agent, or Firm* — Bookoff McAndrews, PLLC

(57) ABSTRACT

This disclosure describes methods and systems for stimulating a respiratory muscle of a patient. The methods herein may include positioning a stimulator adjacent a nerve capable of activating the respiratory muscle; activating the stimulator to cause the respiratory muscle to contract; and ceasing the activation of the stimulator for a period of time. The level and the time of the stimulation may be adjusted for various applications. One or more of the steps in the methods may be repeated. The systems herein may include a stimulator for positioning adjacent a nerve capable of activating the respiratory muscle; a signal generator for providing stimulation energy to the stimulator; a sensor for detecting a response of the respiratory muscle to the stimulation energy; and a controller programmed to control the signal generator for providing stimulation with desired level and time.

22 Claims, 8 Drawing Sheets

(51) Int. Cl.
  *A61N 1/05* (2006.01)
  *A61B 17/00* (2006.01)
  *A61M 25/01* (2006.01)

(52) U.S. Cl.
  CPC .......... *A61B 5/6852* (2013.01); *A61N 1/0551* (2013.01); *A61N 1/0558* (2013.01); *A61N 1/3611* (2013.01); *A61B 17/00234* (2013.01); *A61M 25/0105* (2013.01); *A61N 1/36146* (2013.01)

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | Barchilon |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | Mccormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |

(56) References Cited

U.S. PATENT DOCUMENTS

| | | |
|---|---|---|
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | Mcdaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |

(56) References Cited

U.S. PATENT DOCUMENTS

| | | |
|---|---|---|
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | Mccabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | Mccabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | Mccabe et al. |
| 9,168,377 B2 | 10/2015 | Hoffer |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 10,293,164 B2 | 5/2019 | Nash et al. |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | Mccreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |

(56) References Cited

U.S. PATENT DOCUMENTS

| | | |
|---|---|---|
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0276787 A1 | 10/2013 | Martin et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0073232 A1 | 3/2015 | Ahmad et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0231348 A1 | 8/2015 | Lee et al. |

(56) References Cited

U.S. PATENT DOCUMENTS

| | | |
|---|---|---|
| 2015/0250982 A1 | 9/2015 | Osypka |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De et al. |
| 2015/0374991 A1 | 12/2015 | Morris et al. |
| 2016/0001072 A1 | 1/2016 | Gelfand et al. |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | Mcfarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | 9407564 A2 | 4/1994 |
| WO | 9508357 A1 | 3/1995 |
| WO | 9964105 A1 | 12/1999 |
| WO | 9965561 A1 | 12/1999 |
| WO | 0100273 A1 | 1/2001 |
| WO | 02058785 A1 | 8/2002 |
| WO | 03094855 A1 | 11/2003 |
| WO | 2006110338 A1 | 10/2006 |
| WO | 2006115877 A1 | 11/2006 |
| WO | 2007053508 A1 | 5/2007 |
| WO | 2008092246 A1 | 8/2008 |
| WO | 2008094344 A1 | 8/2008 |
| WO | 2009006337 A1 | 1/2009 |
| WO | 2009134459 A2 | 11/2009 |
| WO | 2010029842 A1 | 3/2010 |
| WO | 2010148412 A1 | 12/2010 |
| WO | 2011158410 A1 | 12/2011 |
| WO | 2012106533 A2 | 8/2012 |
| WO | 2013131187 A1 | 9/2013 |
| WO | 2013188965 A1 | 12/2013 |

OTHER PUBLICATIONS

International Search Report in PCT/US2018/063013, dated Mar. 28, 2019 (3 pages).

Escher, Doris J.W. et al., "Clinical Control of Respiration by Transvenous Phrenic Pacing," American Society for Artificial Internal Organs: Apr. 1968—vol. 14—Issue 1—pp. 192-197.

Ishii, K. et al., "Effects of Bilateral Transvenous Diaphragm Pacing on Hemodynamic Function in Patients after Cardiac Operations," J. Thorac. Cardiovasc. Surg., 1990.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Chinese Search Report for Application No. CN2013/80023357.5, dated Jul. 24, 2015.

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.

Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.

De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.

Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.

European Search Report for Application No. 13758363, dated Nov. 12, 2015.

European Search Report for Application No. EP17169051.4, dated Sep. 8, 2017, 7 pages.

Extended European Search Report for Application No. 15740415.3, dated Jul. 7, 2017.

Frisch S., "A Feasibility Study of a Novel Minimally Invasive Approach for Diaphragm Pacing," Master of Science Thesis, Simon Fraser University, 2009, p. 148.

Furman, S., "Transvenous Stimulation of the Phrenic Nerves," Journal of Thoracic and Cardiovascular Surgery, 1971, vol. 62 (5), pp. 743-751.

Hoffer J.A. et al., "Diaphragm Pacing with Endovascular Electrodes", IFESS 2010—International Functional Electrical Stimulation Society, 15th Anniversary Conference, Vienna, Austria, Sep. 2010.

Japanese Office Action in corresponding Japanese Application No. 2014-560202, dated Oct. 17, 2017, 5 pages.

Evine S., et al., "Rapid disuse atrophy of diaphragm fibers in mechanically ventilated humans," New England Journal of Medicine, 2008, vol. 358, pp. 1327-1335.

Lungpacer: Therapy, News . . . Accessed Dec. 27, 2016.

Martin, A.D. et al., "Inspiratory muscle strength training improves weaning outcome in failure to wean patients: a randomized trial," Critical Care, 2011, vol. 15:R84.

Marcy, T.W. et al., "Diaphragm Pacing for Ventilatory Insufficiency," Journal of Intensive Care Medicine, 1987, vol. 2 (6), pp. 345-353.

Meyyappan R., "Diaphragm Pacing during Controlled Mechanical Ventilation: Pre-Clinical Observations Reveal a Substantial Improvement In Respiratory Mechanics", 17th Biennial Canadian Biomechanics Society Meeting, Burnaby, BC, Jun. 6-9, 2012.

Notification of Reasons for Rejection and English language translation issued in corresponding Japanese Patent Application No. 2015-517565, dated Mar. 28, 2017, 6 pages.

(56) References Cited

OTHER PUBLICATIONS

Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Wanner, A. et al., "Trasvenous Phrenic Nerve Stimulation in Anesthetized Dogs," Journal of Applied Physiology, 1973, vol. 34 (4), pp. 489-494.
Antonica A., et al., "Vagal Control of Lymphocyte Release from Rat Thymus," Journal of the Autonomic Nervous System, Elsevier, vol. 48(3), Aug. 1994, pp. 187-197.
Whaley K., et al., "C2 Synthesis by Human Monocytes is Modulated by a Nicotinic Cholinergic Receptor," Nature, vol. 293, Oct. 15, 1981, pp. 580-582 (and reference page).
Borovikovaa L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.
Borovikovaa L.V., et al., "Vagus Nerve Stimulation Attenuates the Systemic Inflammatory Response to Endotoxin," Nature, Macmillan Magazines Ltd, vol. 405, May 25, 2000, pp. 458-462.
Extended European Search Report for Application No. 14864542.7, dated Jun. 2, 2017, 8 pages.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Japanese Office Action in corresponding Japanese Application No. 2014-560202, dated Dec. 6, 2016, 4 pages.
Kawashima K., et al., "Extraneuronal Cholinergic System in Lymphocytes," Pharmacology & Therapeutics, Elsevier, vol. 86, 2000, pp. 29-48.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.
Nabutovsky, Y., et al., "Lead Design and Initial Applications of a New Lead for Long-Term Endovascular Vagal Stimulation," Pace, Blackwell Publishing, Inc, vol. 30(1), Jan. 2007, pp. S215-S218.
Pavlovic D., et al., "Diaphragm Pacing During Prolonged Mechanical Ventilation of the Lungs could Prevent from Respiratory Muscle Fatigue," Medical Hypothesies, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IκBα in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.
Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

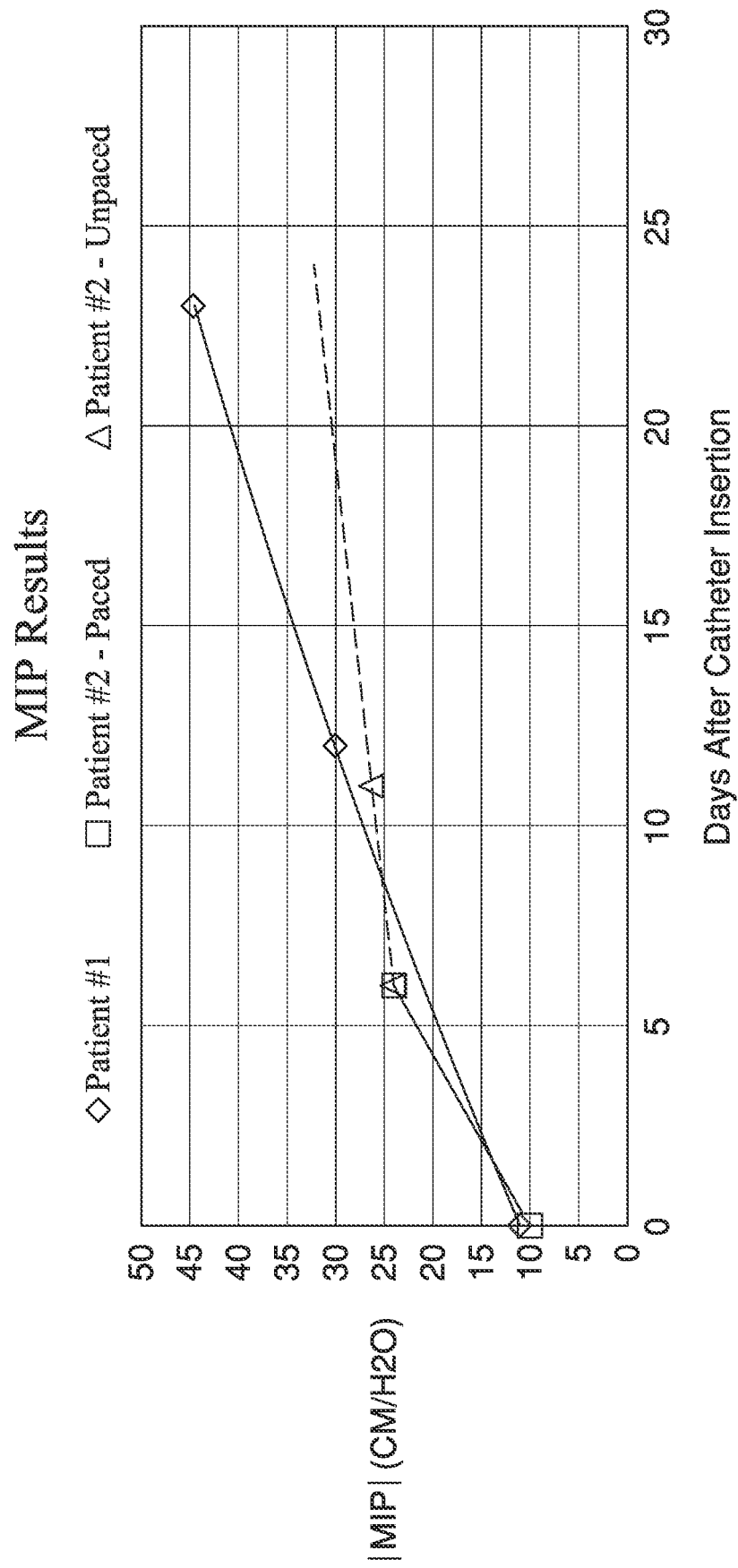

SYSTEMS AND METHODS FOR STRENGTHENING A RESPIRATORY MUSCLE

CROSS-REFERENCE TO RELATED APPLICATIONS

This application is a continuation of U.S. patent application Ser. No. 15/837,519, filed Dec. 11, 2017, which is incorporated herein by reference in its entirety.

INCORPORATION BY REFERENCE

In general, all publications, patent applications, and patents mentioned in this specification are herein incorporated by reference in their entirety to the same extent as if each individual document was specifically individually indicated to be incorporated by reference.

TECHNICAL FIELD

This disclosure relates generally to methods and devices (including systems) for increasing the strength and/or maximum inspiratory force and/or endurance of a respiratory muscle. In some examples, the present disclosure describes methods for increasing the force of a respiratory muscle until a living being (e.g., a patient) is able to breathe without the need for invasive or non-invasive mechanical ventilation, or without the need for other external respiratory support.

In certain examples, the present disclosure describes systems and methods for delivering energy at intervals, or at a low duty cycle, over a period of several days or weeks to respiratory muscles to increase their maximum strength, and/or improve the fatigue threshold until a living being can breathe with reduced, or without, external respiratory support.

In addition, the present disclosure describes systems and methods to mitigate the loss of maximum inspiratory strength of a respiratory muscle in a living being, and more specifically to reduce the degree of such strength loss while a patient is receiving external respiratory support.

BACKGROUND

Critical care patients, particularly those requiring invasive mechanical ventilation (MV), are known to experience higher levels of diaphragm, lung, brain, heart, and other organ injury. The respiratory muscles (e.g., diaphragm, sternocleidomastoid, scalenes, pectoralis minor, external intercostals, internal intercostals, abdominals, quadratus, etc.) are known to rapidly lose mass and strength during MV. The lungs suffer from ventilator-induced trauma; including both high and low pressure injuries. Cognitive effects of MV are believed to be caused by several factors, including aberrant neuro-signaling and inflammatory responses. The heart needs to work harder as: a) respiratory devices such as mechanical ventilators increase blood flow resistance, b) reduced respiratory muscle contraction provides less venous blood flow support, and c) prolonged positive end-expiratory pressure creates blood flow resistance. Each of these is exacerbated the longer that a patient is on MV. To prevent these negative side effects, it is important to keep patients on MV for as short a time as possible. However, rapid respiratory muscle atrophy in MV patients makes it challenging to transition many patients away from a dependency on MV. Today, there are no commercially available options to strengthen the respiratory muscles of critical care patients, particularly for those that are on MV, so that they can quickly regain the ability to breathe without external respiratory support.

In many cases, a patient who is sedated and connected to a mechanical ventilator cannot breathe normally because the central neural drive to the diaphragm and accessory respiratory muscles is often suppressed. Although MV can be a life-saving intervention for patients suffering from respiratory failure, prolonged MV can promote respiratory muscle atrophy. Of particular focus has been the atrophy and contractile dysfunction of the diaphragm resulting from extended periods of time on mechanical ventilation, called ventilator-induced diaphragm atrophy (VIDD). This type of diaphragm injury and accompanying diaphragm weakness are recognized as likely contributors to difficulty in weaning from MV. In a landmark study in brain-dead ICU patients who were kept on MV for just 18 to 69 hours until their donated organs were harvested, the diaphragm muscle fibers had shrunk to less than half of their normal sizes (Levine et al., New England Journal of Medicine, 358: 1327-1335, 2008). Such profound atrophy, when allowed to progress for days or weeks, is considered to be a primary cause for failure to wean from MV in large numbers of MV patients (Demoule et al., Relevance of Ventilator-induced Diaphragm Dysfunction in ICU patients, Clinical Pulmonary Medicine, Volume 19, Number 6 (November 2012)).

It has been demonstrated that even short periods of time on mechanical ventilation can lead to lung injury (e.g., barotrauma, atelectrauma, etc.), lung infection (e.g., pneumonia), brain injury (e.g., cognitive dysfunction, dementia, etc.) and heart injury.

It has been estimated that over 600,000 U.S. patients will be ventilator-dependent and require prolonged mechanical ventilation by the year 2020, at a cost to the US healthcare system of over $60 billion (Zilberberg et al., "Growth in adult prolonged acute mechanical ventilation: implications for healthcare delivery," Crit Care Med., 2008 May, 36(5): 1451-55).

As such, both short and extended time on a mechanical ventilator increases health care costs and greatly increases patient morbidity and mortality. An international, prospective, observational study of MV practices that included 5,183 patients from 20 countries who received MV for greater than 12 hours revealed that patients spend, on average, 40% of their duration of MV in the process of weaning (Esteban et al., Evolution of mechanical ventilation in response to clinical research, Am. J. Respir. Crit. Care Med., 2008 Jan. 15; 177(2):170-7).

The majority of patients treated with MV are readily liberated from ventilator support upon resolution of respiratory failure or recovery from surgery, but approximately one-third encounter challenges with regaining the ability to breathe spontaneously. The prognosis is good for patients who wean successfully at the first attempt (simple wean-ICU mortality ~5%), but is less so for the remaining patients (difficult or prolonged wean-ICU mortality ~25%) (Boles et al., Weaning from mechanical ventilation, Eur. Respir. J., 2007 May; 29(5):1033-56).

Difficulty in weaning from MV is the subject of numerous research efforts around the world, because in many cases patients are able to recover from the condition that originally required them to have MV, but due to the effects of MV they are unable to regain full health.

Some researchers have looked at ways to reduce diaphragm muscle atrophy. Reynolds et al. demonstrated that frequent phrenic nerve stimulation can help mitigate diaphragm muscle atrophy in animal models (Reynolds et al., Mitigation of Ventilator-induced Diaphragm Atrophy by Transvenous Phrenic Nerve Stimulation, Am. J. Respir. Crit. Care Med., 2017 Feb. 1; 195(3):339-348). Lungpacer Medical has disclosed several devices, systems, and methods to prevent diaphragm muscle atrophy.

The literature related to weaning patients from mechanical ventilation has focused on the need for patients to regain diaphragm muscle endurance. One theory has been that a patient needs respiratory muscle endurance to support independent respiration for long periods of time.

SUMMARY

Embodiments of the present disclosure relate to, among other things, systems, devices, and methods for stimulating a respiratory muscle for a small portion of the breaths delivered to or required by a patient in order to strengthen the muscle and/or increase the endurance of the muscle. Each of the embodiments disclosed herein may include one or more of the features described in connection with any of the other disclosed embodiments.

This disclosure includes methods for stimulating a respiratory muscle of a patient. In some aspects, the methods may include: (a) positioning a stimulator adjacent a nerve capable of activating the respiratory muscle; (b) activating the stimulator to cause the respiratory muscle to contract only 100 times or less; (c) ceasing the activation of the stimulator for one or more hours; and (d) repeating steps (b) and (c) at least once. The patient may initiate at least one respiratory muscle contraction of step (b).

In some examples, the methods may further include selecting a pre-determined value of a maximum inspiratory pressure of the patient, and repeating steps (b) and (c) until the maximum inspiratory pressure of the patient increases to the pre-determined value. The pre-determined value may be at least 30 cm $H_2O$. The nerve may be a first nerve, and the respiratory muscle may be a first respiratory muscle, and the method may further include carrying out steps (a) through (d) relative to a second nerve and a second respiratory muscle. The stimulator may include one or more of transvascular electrodes, transdermal electrodes, subcutaneous electrodes, or electrodes configured to be positioned in contact with the nerve.

In some examples, the methods may further include determining a stimulation threshold. The step of determining may include palpating the respiratory muscle. Alternatively or additionally, the step of determining may include observing at least one of a pressure data or a volume data from an external respiratory support system. The methods may further include using a mechanical ventilator to provide respiratory support to the patient during at least a portion of step (b).

In some aspects, the methods for stimulating a respiratory muscle of a patient may include (a) positioning a stimulator adjacent a nerve capable of activating the respiratory muscle; (b) first activating the stimulator to cause the respiratory muscle to contract only 100 times or less; (c) ceasing the first activation of the stimulator for at least 30 seconds; (d) after step (c), second activating the stimulator to cause the respiratory muscle to contract only 100 times or less; (e) ceasing the second activation of the stimulator for one or more hours; and (f) repeating steps (b) through (e) at least once. The nerve may be at least one of a phrenic nerve or a vagus nerve. In one example, step (b) may include 100 or less stimulations corresponding to the 100 or less contractions of the respiratory muscle, and step (b) may include adjusting at least one stimulation parameter between a first stimulation of the 100 or less stimulations and a second stimulation of the 100 or less stimulations.

In some examples, the nerve may be a first nerve, the respiratory muscle may be a first respiratory muscle, and the stimulator may include a first set of electrodes positioned adjacent the first nerve and a second set of electrodes positioned adjacent a second nerve capable of activating either the first respiratory muscle or a second respiratory muscle, and the method may further include: (g) first activating the second set of electrodes to cause the first or second respiratory muscle to contract only 100 times or less; (h) ceasing the first activation of the second set of electrodes for at least 30 seconds; (i) after step (h), second activating the second set of electrodes to cause the first or second respiratory muscle to contract only 100 times or less; (j) ceasing the second activation of the second set of electrodes for one or more hours; and (k) repeating steps (g)-(j) at least once. Steps (b) and (g) may occur at the same time.

In some examples, the methods may further include sensing a contraction of the respiratory muscle; and adjusting at least one stimulation parameter to achieve a desired contraction of the respiratory muscle. The steps of sensing and adjusting may be carried out automatically by a controller. The controller may be implanted in the patient.

In some aspects, the methods for stimulating a respiratory muscle of a patient may include (a) positioning a stimulator adjacent a nerve capable of activating a respiratory muscle; and (b) activating the stimulator to cause the respiratory muscle to contract for no more than 20% of the breaths taken by, or delivered to, the patient in a 24-hour period. Step (b) may include activating the stimulator to cause the respiratory muscle to contract for no more than 10% of the breaths taken by, or delivered to, the patient in the 24-hour period.

In some examples, the methods may further include providing external respiratory support for at least 60% of the patient's breaths in the 24-hour period; and subsequent to step (b), at least one of reducing a pressure provided by the external respiratory support or reducing a percentage of breaths assisted by the external respiratory support. The external respiratory support may include at least one of mechanical ventilation, BiPAP, CPAP, or nasal cannula oxygenation. In some examples, the stimulator may include a plurality of electrodes, and the method may further include using a controller to automatically select an electrode combination from the plurality of electrodes for stimulating the nerve and causing the respiratory muscle to contract. In some examples, the methods may further include using a sensor to measure a physiological parameter of the patient, wherein the physiological parameter may include at least one of a breath rate, a heart rate, an ECG, a temperature, a motion, a blood oxygen level, a blood $CO_2$ level, or an air flow.

In some aspects, the methods for stimulating a respiratory muscle of a patient may include (a) positioning a stimulator adjacent a nerve capable of activating the respiratory muscle; (b) providing external respiratory support to the patient; (c) providing extracorporeal membrane oxygenation to the patient to at least one of remove $CO_2$ or add oxygen to the patient's blood; and (d) activating the stimulator to cause the respiratory muscle to contract for no more than five cumulative hours in a 24-hour period. At least some stimulations during the activation of the stimulator in step (d) may occur during inspiration periods of the external respiratory support provided in step (b).

In some examples, a first time period between a first pair of consecutive stimulations during the activation of the stimulator in step (d) may be different than a second time period between a second pair of consecutive stimulations during the activation of the stimulator in step (d). A plurality of electrodes of the stimulator may be positioned within the patient through a percutaneous incision. A plurality of electrodes of the stimulator may be positioned external to the patient.

In some examples, the methods may alternatively or additionally include: delivering at least one drug to the patient prior to step (d); or using a sensor to detect an inflammatory agent.

In some aspects, methods for stimulating a respiratory muscle of a patient may include (a) positioning a stimulator adjacent a nerve capable of activating the respiratory muscle; (b) providing external respiratory support for at least 90% of the patient's breaths in a 24-hour period; (c) activating the stimulator to cause the respiratory muscle to contract for no more than five cumulative hours in a 24-hour period; (d) repeating steps (b) and (c) for 48 hours; and (e) removing the external respiratory support from the patient. The methods may further include repeating step (c) for at least one day after removing the external respiratory support from the patient.

In some aspects, the methods for stimulating a respiratory muscle of a patient may include: (a) positioning a stimulator adjacent a nerve capable of activating the respiratory muscle; and (b) activating the stimulator to cause the respiratory muscle to contract for a cumulative duration of 2 hours or less per day while the patient is breathing.

In some aspects, the methods for stimulating a respiratory muscle of a patient may include: (a) positioning a stimulator adjacent a nerve or muscle capable of activating a respiratory muscle; (b) providing external respiratory support for at least 90% of a patient's breaths in a 24-hour period (c) activating the stimulator to cause the respiratory muscle to contract; (d) varying at least one of a stimulation intensity or a stimulation rate; and (e) removing the external respiratory support from the patient.

This disclosure further includes systems for stimulating a respiratory muscle of a patient. In some examples, the systems may include: a stimulator for positioning adjacent a nerve capable of activating the respiratory muscle; a signal generator for providing stimulation energy to the stimulator; a sensor for detecting a response of the respiratory muscle to the stimulation energy; and a controller programmed to: (i) cause the signal generator to provide stimulation energy to the stimulator to cause only 100 or less contractions of the respiratory muscle; and (ii) cause the signal generator to provide a period of one hour or more after causing the 100 or less contractions. The stimulator may include one or more of: nerve stimulation electrodes, endotracheal electrodes, endoesophageal electrodes, intravascular electrodes, transcutaneous electrodes, intracutaneous electrodes, electromagnetic beam electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, or probe electrodes. The stimulation energy may be delivered by an energy form that includes at least one of mechanical, electrical, ultrasonic, photonic, or electromagnetic energy. In some examples, the systems may further include a switch communicably coupled to the controller, wherein the switch includes one of a hand switch, a foot switch, a touch screen, a voice-activated switch, or a remote switch It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF DRAWINGS

The accompanying drawings, which are incorporated in and constitute a part of this specification, illustrate non-limiting embodiments of the present disclosure and together with the description, serve to explain the principles of the disclosure.

FIG. 6 illustrates data related to the increase in strength of respiratory muscles for two exemplary living beings receiving therapy using the systems and methods of one example of this disclosure.

DETAILED DESCRIPTION

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative, rather than a restrictive, sense.

As described above in the Background section, endurance of respiratory muscles has been a focus of previous research. This disclosure relates in part to increasing the maximum respiratory muscle strength, which also is useful for achieving successful independent respiration. To date, there remains an unmet need for an easy-to-use device, system, and method to rapidly and efficiently build, or maintain, respiratory muscle strength and/or endurance to reverse, or to limit, the muscle injury often experienced when patients are dependent on external respiratory support such as mechanical ventilation.

This disclosure includes systems and methods that may provide a rapid increase in the maximum inspiratory strength and/or endurance of patients with weakened respiratory muscles, and help wean them from external respiratory support. The systems may involve the delivery of energy-based therapy to the patients to activate respiratory muscle(s) for a relatively small percentage of the breaths taken by, or delivered by external means to, the patient each day. Therapy can be delivered as intermittently as 25% of the breaths taken per day, or in some cases less than 10%, less than 1%, or less than 0.2% of the breaths taken by, or delivered by external means to, the patient each day. The systems and methods can automatically stimulate the desired muscles, either directly or indirectly (e.g., via nerves), at a determined interval, frequency, or duty cycle. The therapy can be activated automatically at predetermined intervals or conditions, activated by a healthcare professional, or activated by the patients themselves, as needed. The therapy may be designed to increase, or preserve, the respiratory muscle strength and/or endurance for patients dependent on external respiratory support.

In general, embodiments of this disclosure relate to medical devices and methods for electrically stimulating a patient's nerves to activate a respiratory muscle at infrequent intervals. In some cases, the muscles may be strengthened until the patient can breathe without external respiratory support.

Figure 1:
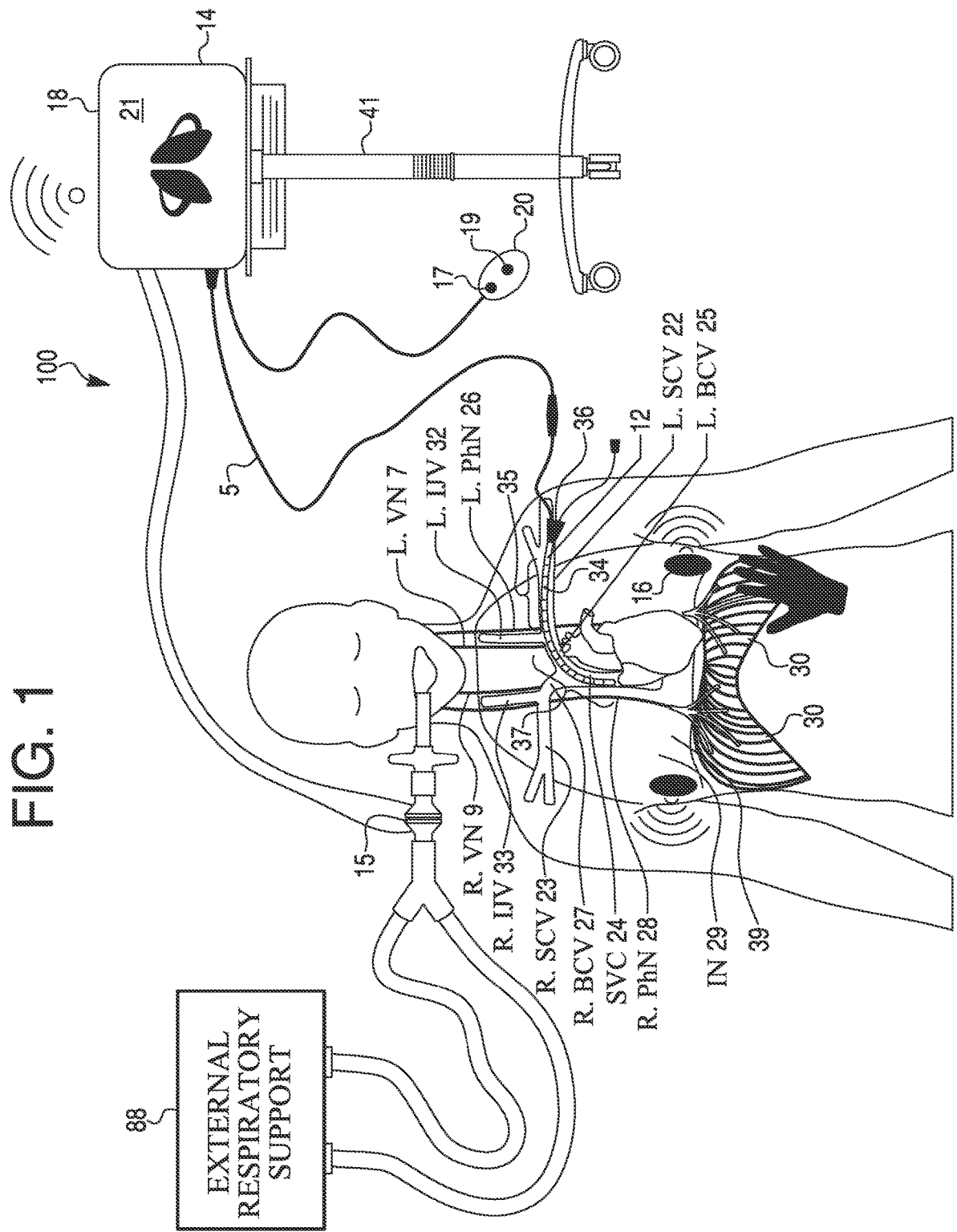
FIG. 1 illustrates the anatomy of selected nerves and blood vessels in a person's neck and upper torso, the diaphragm and intercostal respiratory muscles, an exemplary stimulation catheter placed in one vein, a control unit, a sensor (e.g., motion sensor, airflow sensor, and/or pressure sensor), an exemplary remote control device, a graphical user interface, a pulse generator, and an external respiratory support device, according to an exemplary embodiment.

Referring to FIG. 1, the systems described herein may include several components, including: a stimulator having one or more electrodes or electrode assemblies, such as a transvascular nerve stimulation catheter 12 including stimulation electrodes (FIG. 1) or transcutaneous stimulation array 13 (FIG. 2); a signal generator 14 to provide stimulation energy to the electrode assemblies; one or more sensors 16, or means for sensing, to sense a condition of the patient and inform adjustments to the stimulation signals and/or external respiratory support; and a control unit 18 to manage the parameters associated with the delivery of the stimulation signals to the electrodes. In some embodiments, the system may incorporate a remote controller 20, a graphical user interface (GUI) 21, a touchscreen (e.g., as part of GUI 21), a hand-held controller (e.g., remote controller 20), a keyboard, a computer (e.g., control unit 18), a smart phone, a tablet, or another input device.

In some examples, the stimulator devices (e.g., catheter 12) are readily applied to, or inserted into, the patient, temporary, and easily removed from the patient without the need for surgery at a later time. The stimulator, such as catheter 12 or other stimulation array, may be positioned internal to the patient via a percutaneous incision in the patient's neck. In some cases, the stimulator may be inserted proximate subclavian, femoral, or radial regions of the patient. In other examples, as described herein, the stimulator may be positioned external to the patient.

The various system components described herein may be combined and used together in any logical arrangement. Furthermore, individual features or elements of any described example may be combined with or used in connection with the individual features or elements of other embodiments. The various examples may further be used in different contexts than those specifically described herein. For example, the disclosed electrode structures may be combined or used in combination with various deployment systems known in the art for various diagnostic and/or therapeutic applications.

FIG. 1 further illustrates the anatomy of the neck and chest and, in particular, the relative locations of the left and right phrenic nerves (L. PhN 26 and R. PhN 28), vagus nerves (L. VN 7 and R. VN 9), left and right internal jugular veins (L. IJV 32 and R. IJV 33), left and right brachiocephalic veins (L. BCV 25 and R. BCV 27), left and right subclavian veins (L. SCV 22 and R. SCV 23), the superior vena cava (SVC 24), and intercostal nerves (IN 29). FIG. 1 further illustrates a diaphragm 30 and intercostal muscles 39. The phrenic nerves 26, 28 run approximately perpendicular to and close to the subclavian veins 22, 23, or in some cases brachiocephalic veins 25, 27 near the junctions of the internal jugular veins 32, 33 and the brachiocephalic veins 25, 27. Each phrenic nerve 26, 28 may have more than one branch. The branches may join together at variable locations ranging from the neck region to the chest region below the junctions between the internal jugular veins 32, 33 and the brachiocephalic veins 25, 27. In the latter case, branches of the phrenic nerves 26, 28 on either side of the body may course on opposite sides of the brachiocephalic veins 25, 27. The right phrenic nerve 28 may include branches that course on either side of the superior vena cava 24. The left and right phrenic nerves 26, 28 extend respectively to left and right hem i-diaphragms.

FIG. 1 also illustrates a medical system 100 that includes transvascular nerve stimulation catheter 12 and control unit 18. Catheter 12 may include a plurality of electrodes 34. Catheter 12 may be operably connected (e.g., hardwired via cable 5, wireless, etc.) to control unit 18. Control unit 18 may be programmed to perform any of the functions described herein in connection with system 100. In some embodiments, control unit 18 may include a remote controller 20 to allow a patient or health professional to control operation of control unit 18 at a distance from the control unit 18. The remote controller 20 may include a handheld device, as illustrated in FIG. 1. In some examples, remote controller 20 may include a footswitch/pedal, a voice-activated, touch-activated, or pressure-activated switch, or any other form of a remote actuator. The control unit 18 may include a touch screen and may be supported by a cart 41.

The remote controller 20 may include buttons 17, 19 that can be pressed by a patient or other user to control breathing patterns. In one example, pressing one of buttons 17, 19 can initiate a "sigh" breath, which may cause a greater volume of air to enter the patient's lungs than in a previous breath. A sigh breath may result when electrodes 34 of catheter 12 are directed to stimulate one or more of the phrenic nerves 26, 28 at a higher level than a normal breath (e.g., a stimulation train having a longer duration of stimulation or having pulses with a higher amplitude, pulse width, or frequency). Higher amplitude stimulation pulses can recruit additional nerve fibers, which in turn can engage additional muscle fibers to cause stronger and/or deeper muscle contractions. Extended pulse widths or extended durations of the stimulation train can deliver stimulation over longer periods of time to extend the duration of the muscle contractions. In the case of diaphragm muscle stimulation, longer pulse widths or extended duration of stimulation (train of pulses) have the potential to help expand the lower lung lobes by providing greater or extended negative pressure around the outside of the lungs. Such negative pressure has the potential to help prevent or mitigate a form of low pressure lung injury known as atelectasis. The increase in stimulation frequency can result in a more forceful contraction of the diaphragm 30. The increased stimulation (e.g., higher amplitude, pulse width, stimulation duration, or frequency) of the one or more phrenic nerves 26, 28 may result in a more forceful contraction of the diaphragm 30, causing the patient to inhale a greater volume of air, thereby providing a greater amount of oxygen to the patient. Sigh breaths may increase patient comfort.

In other examples, buttons 17, 19 may allow the patient or other user to start and stop stimulation therapy, or to increase or decrease stimulation parameters, including stimulation charge (amplitude×pulse width), frequency of pulses in a stimulation train, or breath rate. LED indicators or a small LCD screen (not shown) on the remote controller 20 or control unit 18 may provide other information to guide or inform the operator regarding the stimulation parameters, the feedback from the system sensors, or the condition of the patient.

Alternatively, a control unit having the functionality of control unit 18 can be implanted in the patient, along with catheter 12. In this example, remote controller 20 and a programmer (not shown) may communicate with the implanted control unit wirelessly. Each of the programmer, the implanted control unit, and remote controller 20 may include a wireless transceiver so that each of the three components can communicate wirelessly with each other. The implanted control unit may include all of the electronics, software, and functioning logic necessary to perform the functions described herein. Implanting the control unit may allow catheter 12 to function as a permanent breathing pacemaker. A programmer may allow the patient or health professional to modify or otherwise program the nerve stimulation or sensing parameters. In some examples, remote controller 20 may be used as described in connection with FIGS. 1 and 2. In other examples, remote controller 20 may be in the form of a smartphone, tablet, watch, or other suitable input device.

In yet another additional or alternative example, the control unit of system 100 may be portable. The portable control unit may include all of the functionality of control unit 18 of FIG. 1, but it may be carried by a patient or other user to provide the patient with more mobility and may be disconnected from the cart 41. In addition to carrying the portable control unit, the patient can wear the control unit on a belt, on other articles of clothing, or around his/her neck, for example. In other examples, the portable control unit may be mounted to a patient's bed to minimize the footprint of system 100 in the area around the patient, or to provide portable muscle stimulation in the event a bed-ridden patient needs to be transported or moved to another location.

The distal tip of catheter 12 may be a tapered distal end portion of catheter 12 and may have a smaller circumference than the body of catheter 12. The distal tip may be open at the distal end to allow a guide wire to pass through and distally beyond catheter 12. And, the distal tip may be softer than other portions of catheter 12, be atraumatic, and have rounded edges. Catheter 12 also may have two ports or openings in the sidewall of the catheter. A first opening may be located at a mid-portion of catheter 12 and a second opening may be located near a proximal end of catheter 12. Each opening may be in fluid communication with respective lumens in catheter 12, through which fluid can be infused. The fluid may exit the ports to be delivered into a blood vessel.

During use, a proximal portion of catheter 12 may be positioned in left subclavian vein 22, and a distal portion of catheter 12 may be positioned in superior vena cava 24. Positioned in this manner, electrodes 34 on the proximal portion of catheter 12 may be positioned proximate left phrenic nerve 26, and electrodes 34 on the distal portion of catheter 12 may be positioned proximate right phrenic nerve 28. As an alternative insertion site, catheter 12 may be inserted into left jugular vein 32 and superior vena cava 24, such that the proximal electrodes are positioned to stimulate left phrenic nerve 26 and the distal electrodes are positioned to stimulate right phrenic nerve 28.

Left and right phrenic nerves 26, 28 may innervate diaphragm 30. Accordingly, catheter 12 may be positioned to electrically stimulate one or both of the left and right phrenic nerves 26, 28 to cause contraction of the diaphragm muscle 30 to initiate or support a patient breath.

In further examples, catheter 12 can be placed into and advanced through other vessels providing access to the locations adjacent the target nerve(s) (e.g., phrenic nerves), such as: the jugular, axillary, cephalic, cardiophrenic, brachial, or radial veins. In addition, the stimulator (e.g., catheter 12 or array 13) may use other forms of stimulation energy, such as ultrasound, to activate the target nerves. In some examples, the system 100 can target other respiratory muscles (e.g., intercostal) either in addition to, or alternatively to, the diaphragm 30. The energy can be delivered via one or more types of electrodes/methods including transvascular electrodes, subcutaneous electrodes, electrodes configured to be positioned in contact with the nerve (e.g., nerve cuffs), transdermal electrodes/stimulation, or other techniques known in the field.

The nerve stimulation systems and methods described herein may reduce or eliminate the need for a patient to receive external respiratory support. External respiratory support 88 in FIGS. 1 and 2 can include any devices or methods to help correct or otherwise enhance blood gases and/or reduce the work of breathing of a patient. Some non-limiting examples include mechanical ventilation, non-invasive ventilation (NIV), CPAP, BiPAP, nasal cannula oxygenation, DPS (Synapse, Avery, etc.), and ECMO, as described below.

Mechanical ventilation may refer to use of a ventilator to assist or replace spontaneous breathing. Mechanical ventilation is termed "invasive" if it involves any instrument penetrating through the mouth (such as an endotracheal tube) or the skin (such as a tracheostomy tube). There are two main types of mechanical ventilation: positive pressure ventilation, where air (or another gas mix) is forced into the trachea via positive pressure, and negative pressure ventilation, where air is drawn into (e.g., sucked into) the lungs (e.g., iron lung, etc.). There are many modes of mechanical ventilation. Mechanical ventilation may be indicated when the patient's spontaneous ventilation is unable to provide effective gas exchange in the lungs.

Ventilation also can be provided via a laryngeal mask airway (e.g., laryngeal mask), which is designed to keep a patient's airway open during anesthesia or unconsciousness. It is often referred to as a type of supraglottic airway. A laryngeal mask may include an airway tube that connects to an elliptical mask with a cuff, which is inserted through the patient's mouth and down the windpipe. Once deployed, the device forms an airtight seal on top of the glottis (unlike tracheal tubes, which pass through the glottis) to provide a secure or stable airway.

Non-invasive ventilation (NIV) is the use of airway support administered through a face (e.g., oral, nasal, nasal-oral) mask/cannula instead of an endotracheal tube. Inhaled gases are given with positive end-expiratory pressure, often with pressure support or with assist control ventilation at a set tidal volume and rate. This type of treatment is termed "non-invasive" because it is delivered with a mask that is tightly fitted to the face, but without a need for tracheal intubation.

Continuous positive airway pressure (CPAP) is a form of positive airway pressure ventilation, which applies mild air pressure on a continuous basis to keep the airways continuously open. CPAP may be used for patients who are able to breathe spontaneously on their own but may require a level of pressure support. It is an alternative to positive end-expiratory pressure (PEEP). Both modalities stent the lungs' alveoli open and therefore help recruit more of the lung's surface area for ventilation. PEEP generally refers to devices that impose positive pressure only at the end of an exhalation. CPAP devices apply continuous positive airway pressure throughout the breathing cycle. Thus, the ventilator itself does not cycle during CPAP, no additional pressure above the level of CPAP is provided, and patients must initiate each breath on their own.

Bilevel Positive Airway Pressure (BiPAP) therapy is very similar in function and design to CPAP. BiPAPs can also be set to include a breath timing feature that measures the amount of breaths per minute a person should be taking. If the time between breaths exceeds the set limit, the machine can force the person to breath by temporarily increasing the air pressure. The main difference between BiPAP and CPAP machines is that BiPAP machines generally have two pressure settings: the prescribed pressure for inhalation (ipap), and a lower pressure for exhalation (epap). The dual settings allow the patient to move more air in and out of their lungs.

Extracorporeal membrane oxygenation (ECMO), which is also known as extracorporeal life support (ECLS), is an extracorporeal technique to provide prolonged cardiac and respiratory support to patients whose heart and lungs are unable to provide an adequate amount of gas exchange. The technology for ECMO is similar to that used during cardio-pulmonary bypass, which is typically used to provide shorter-term support. During ECMO, blood is removed from the person's body and passed through a device which removes carbon dioxide and provides oxygen to red blood cells. Long term ECMO patients can often develop respiratory muscle weakness because of muscle inactivity and other causes. Certain therapy methods described herein may include delivering stimulation therapy to a patient receiving both ECMO and another form of external respiratory support. Certain therapy methods in this disclosure may utilize ECMO devices, which may include a stimulation array, to deliver the described therapy.

Referring still to FIG. 1, catheter 12 may include a stimulation array comprising a plurality of electrodes 34 or other energy delivery elements. In one example, electrodes 34 may be surface electrodes located on an outer wall of catheter 12. In another example, electrodes 34 may be positioned radially inward relative to the outer wall of catheter 12 (e.g., exposed through openings in the outer wall). In yet another example, the electrodes 34 may include printed electrodes as described in U.S. Pat. No. 9,242,088, which is incorporated by reference herein (see below).

Electrodes 34 may extend partially around the circumference of catheter 12. This "partial" electrode configuration may allow electrodes 34 to target a desired nerve for stimulation, while minimizing application of electrical charge to undesired areas of the patient's anatomy (e.g., other nerves or the heart). As shown in FIG. 1, catheter 12 may include a proximal set 35 of electrodes 34 configured to be positioned proximate to and stimulate left phrenic nerve 26 and a distal set 37 of electrodes 34 configured to be positioned proximate to and stimulate right phrenic nerve 28. Electrodes 34 may be arranged in rows extending along the length of catheter 12. In one example, proximal set 35 may include two rows of electrodes 34 extending parallel to a longitudinal axis of catheter 12, and distal set 37 may include two rows of electrodes 34 extending parallel to a longitudinal axis of catheter 12.

Furthermore, the catheters described herein may include any features of the nerve stimulation devices and sensing devices described in the following documents, which are all incorporated by reference herein in their entireties: U.S. Pat. No. 8,571,662 (titled "Transvascular Nerve Stimulation Apparatus and Methods," issued Oct. 29, 2013); U.S. Pat. No. 9,242,088 (titled "Apparatus and Methods for Assisted Breathing by Transvascular Nerve Stimulation," issued Jan. 26, 2016); U.S. Pat. No. 9,333,363 (titled "Systems and Related Methods for Optimization of Multi-Electrode Nerve Pacing," issued May 10, 2016); U.S. application Ser. No. 14/383,285 (titled "Transvascular Nerve Stimulation Apparatus and Methods," filed Sep. 5, 2014); U.S. application Ser. No. 14/410,022 (titled "Transvascular Diaphragm Pacing Systems and Methods of Use," filed Dec. 19, 2014); U.S. application Ser. No. 15/606,867 (titled "Apparatus And Methods For Assisted Breathing By Transvascular Nerve Stimulation," filed May 26, 2017); or U.S. application Ser. No. 15/666,989 (titled "Systems And Methods For Intravascular Catheter Positioning and/or Nerve Stimulation," filed Aug. 2, 2017). In addition, the control units described herein can have any of the functionality of the control units described in the above-referenced patent documents (e.g., the control units described herein can implement the methods of nerve stimulation described in the incorporated documents).

During nerve stimulation, one or more electrodes 34 may be selected from the proximal set 35 for stimulation of left phrenic nerve 26, and one or more electrodes 34 may be selected from the distal set 37 for stimulation of right phrenic nerve 28. Catheter 12 may stimulate nerves using monopolar, bipolar, or tripolar electrode combinations, or using any other suitable combination of electrodes 34. In some examples, a second or third group of electrodes can be used to stimulate other respiratory muscles. In general, a stimulator or a stimulation array may include multiple sets of electrodes, with each set being configured to stimulate either the same or different nerves or muscles. When multiple nerves or muscles are being stimulated, the controllers and sensors described herein may be used to coordinate stimulation to achieve the desired muscle activation, breath, or level of respiratory support.

Catheter 12 may further include one or more lumens. Each lumen may extend from a proximal end of catheter 12 to a distal end of catheter 12, or to a location proximate the distal end of catheter 12. In some examples, lumens may contain or be fluidly connected to sensors, such as blood gas sensors, electrical sensors, motion sensors, flow sensors, or pressure sensors. In some examples, catheter 12 may include three lumens (not shown) that may connect with extension lumens (not shown) that extend proximally from hub 36. Any lumens within catheter 12 may terminate in one or more distal ports (not shown) either at the distal end of catheter 12 or in a sidewall of catheter 12. In one example, the lumens may be used to transport fluid to and from the patient, such as to deliver medications or withdraw blood or other bodily fluids, to remove $CO_2$, and/or to infuse oxygen. In other examples, these lumens may be used to hold a guidewire, stiffening wire, optical fiber camera, sensors, or other medical devices.

Catheter 12, or other stimulation devices of this disclosure, may incorporate markings or other indicators on its exterior to help guide the positioning and orientation of the device. Catheter 12, or other stimulation devices of this disclosure, may also include internal indicators (e.g., radiopaque markers, contrast material such as barium sulfate, echogenic markers, etc.) visible by x-ray, ultrasound or other imagining technique to assist with positioning the stimulator in the desired location. Catheter 12 may include any combination of the features described herein. Accordingly, the features of catheter 12 are not limited to the specific combination shown in FIG. 1.

Referring still to FIG. 1, a hub 36 may be connected to the proximal end of catheter 12. Hub 36 may include a conductive surface and can act as a reference electrode during monopolar stimulation or sensing. In some embodiments, hub 36 may be sutured on a patient's skin. In addition, hub 36 may be used as an ECG electrode.

In one example, the distal or proximal portion of catheter 12 may be configured to assume a helical shape when positioned within the patient to help anchor catheter 12 to the vessel wall or to stabilize catheter 12 during nerve stimulation. The helical shape may position electrodes 34 at different radial positions within the vessel and relative to target nerves. Selecting electrodes 34 at different radial positions within the vessel (whether or not due to any helical shape), or at different distances from the target neve (whether or not due to any helical shape), may be useful for nerve stimulation. For example, in certain instances it may be desirable to stimulate the nerve with electrodes 34 that are closer to the nerve (e.g., to obtain a stronger respiratory muscle response), and in other instances it may be desirable to stimulate the nerve with electrodes 34 that are farther away from the nerve (e.g., to obtain a weaker respiratory muscle response, or prevent stimulation of unwanted nerves).

The electrodes 34 of catheter 12 may be formed by conductive inks (such as silver, gold, graphine or carbon flakes suspended in polymer or other media) printed on the surface of catheter 12, as described in U.S. Pat. No. 9,242,088, incorporated by reference herein (see above). These conductive inks may be deposited and adhered directly onto catheter 12 and sealed, except for the exposed electrodes 34, with an outer polyurethane or other flexible insulative film/ material.

When electrical charge is delivered to the phrenic nerves, the diaphragm muscles may contract and generate negative pressure in the thoracic cavity. The lungs then expand to draw in a volume of air. This contraction of diaphragm muscles can be sensed manually by palpation or by placing a hand on the thoracic cavity, as shown in FIG. 1. Alternatively, the breathing activity can be sensed by placing an airflow or airway pressure sensor in the breathing circuit or placing sensors 16, such as accelerometers or a gyroscope, on the surface of the skin at the thoracic region, as shown in FIG. 1. Sensors 16 can be hard wired to control unit 18 or can be connected using wireless transmitters and receivers.

In some examples, catheter 12 can be easily inserted into (or secured relative to) the patient. In many embodiments, catheter 12 can be readily removed from the patient's body when desired without the need for surgery. For example, catheter 12 of FIG. 1 can be simply withdrawn once the patient is breathing independently.

Figure 2:
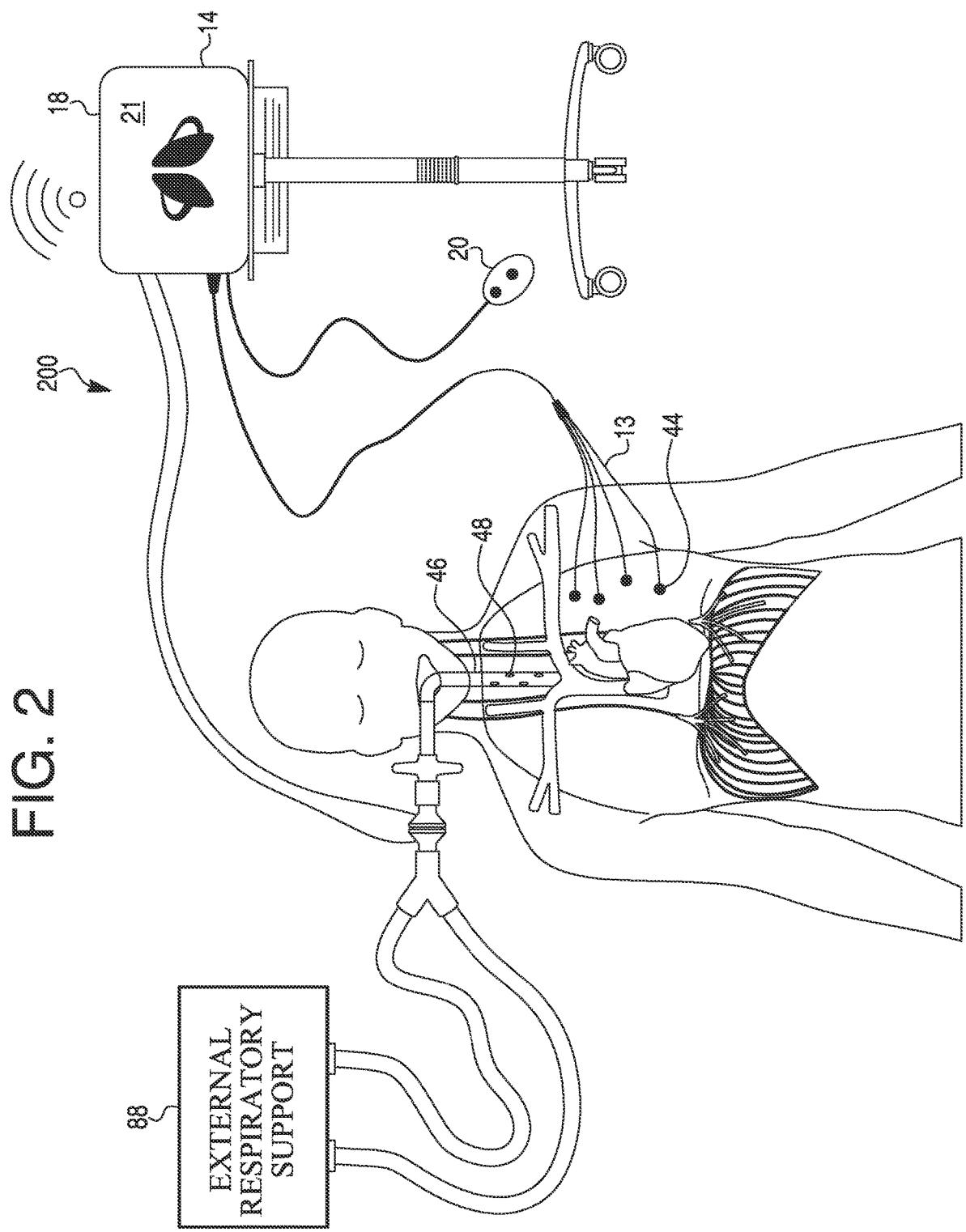
FIG. 2 illustrates the anatomy of respiratory muscles of the torso, a transdermal respiratory muscle stimulation array of electrodes placed upon the skin of the patient over the intercostal muscles, transesophageal electrodes, and an external respiratory support device, according to an exemplary embodiment.

FIG. 2 illustrates the anatomy of the neck and chest, similar to FIG. 1. FIG. 2 also schematically illustrates the region of the intercostal muscles. The intercostal muscles include several groups of muscles that run between the ribs and that help form and move the chest wall. The intercostal muscles are involved in the mechanical aspect of breathing. These muscles help expand and shrink the size of the chest cavity to facilitate breathing.

FIG. 2 illustrates a medical system 200 that includes a transcutaneous electrode array 13. The array 13 includes a series of electrodes 44 placed on the surface of the skin of the patient in close proximity to the intercostal muscles. Electrodes 44 may have any suitable shape and size, and may serve a variety of functions, such as sensing electrical activity and stimulating the muscles or nerves through the skin. Electrodes 44 can include stainless steel, conductive carbon fiber loaded ABS plastic, silver/silver chloride ionic compound, or any other suitable material, or any combination of materials. Each electrode 44 can be covered by a polymeric or elastomeric film that may include an adhesive to attach the electrode 44 to skin. Alternatively, the electrode film may contain electrolyte gel for better conduction of the signals. In some embodiments, other forms of electrodes, for example subcutaneous or needle electrodes, can be used to stimulate intercostal muscles, or the system may use other forms of stimulation energy, such as ultrasound, to activate the target nerves or muscles.

FIG. 2 further illustrates a transesophageal tube 46 with electrodes 48 on the tube and/or on an inflatable balloon surrounding all or part of tube 46. Electrodes 48 can be printed on the surface of tube 46 (or the balloon) using conductive ink such as silver ink, gold ink, graphene ink, or carbon-based ink. Alternatively, electrodes 48 can be formed by using an adhesive to secure the electrode material, such as platinum iridium, stainless steel, titanium, or similar material, to tube 46 and connecting electrodes 48 to control unit 18 with one or more conductive wires. Electrodes 48 can be used to sense the signals from the phrenic nerves or vagus nerves or some other neurological element. Electrodes 48 can also be used to stimulate the nerves, such as, for example, at least one of vagus nerves, phrenic nerves, or sympathetic ganglia.

Additionally or alternatively, system 200 of FIG. 2 can include a catheter with electrodes and/or sensors, as described in the FIG. 1. To restore negative pressure ventilation, system 200 can stimulate one or both phrenic nerves to activate the diaphragm muscles, along with stimulating the intercostal muscles, to create a negative pressure in the thoracic cavity. The system may receive feedback by sensing the phrenic or vagus activity from one of the electrodes on the intravascular catheter (if used) or transesophageal tube 46. Feedback from nerve activity may be used to determine the stimulation parameters required to sustain proper ventilation and whether adjustments to the stimulation parameters are needed. The system can also receive feedback from any other suitable sensor to determine the appropriate stimulation parameters. One or more of each of the following sensors may be included in either system 100 or system 200: an airflow sensor, an airway pressure sensor, an accelerometer, a gyroscope, a blood gas sensor, or a sensor to detect an inflammatory agent. In some examples, system 100 or system 200 may include a sensor to detect an inflammatory agent. Examples of such inflammatory agents include, but are not limited to, C-reactive protein, nitric oxide, or biomarkers for an inflammatory disease (e.g., inflammatory bowel disease).

Figure 3:
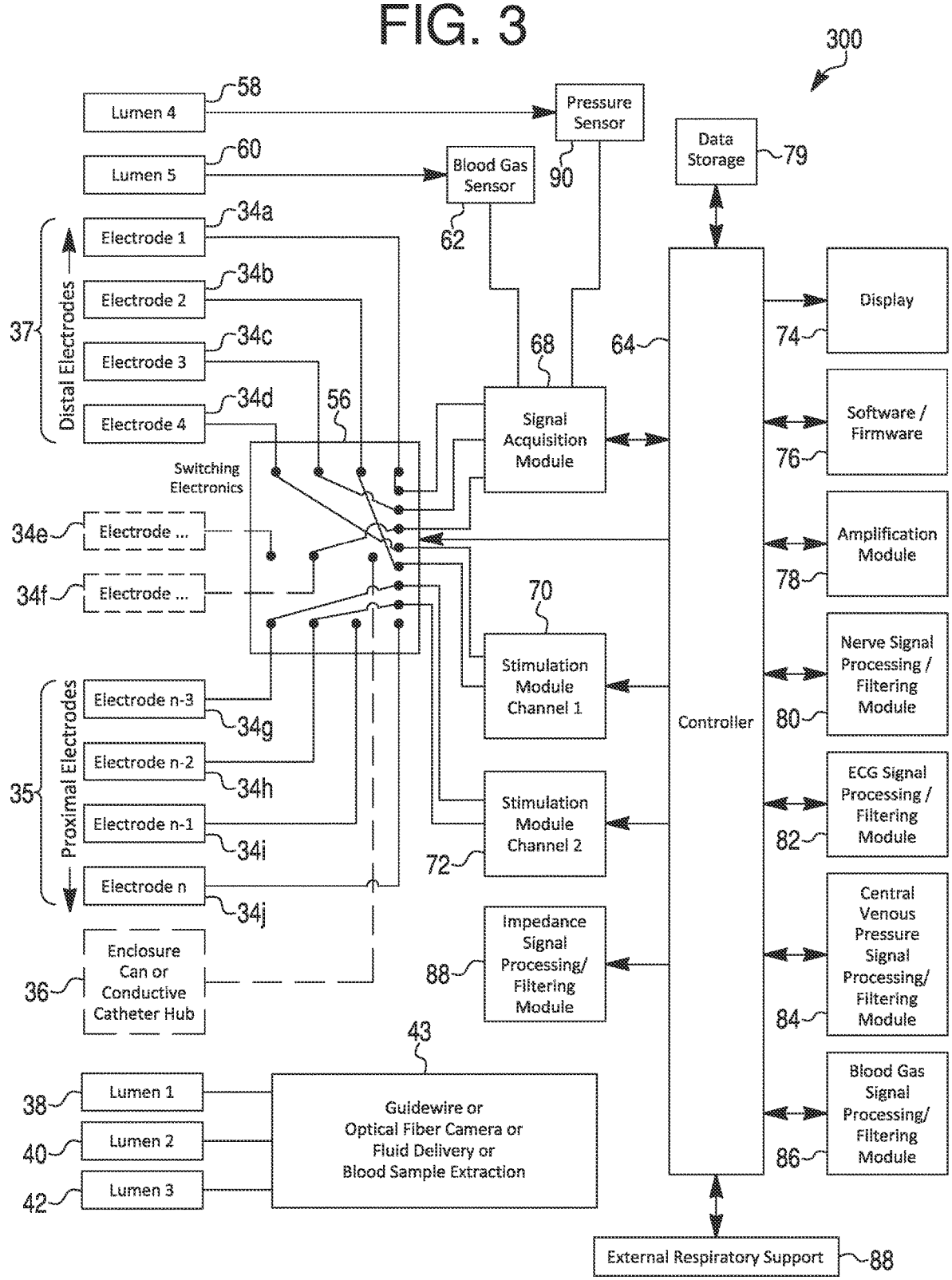
FIG. 3 illustrates a block diagram of a respiratory muscle stimulation system having an intravascular catheter and a controller, according to an exemplary embodiment.

FIG. 3 illustrates a block diagram of various components of an exemplary stimulation therapy system 300. A stimulator, such as catheter 12 or array 13, may have any number of electrodes (illustrated as electrodes 34a-34j). If the electrodes are included on a catheter, the catheter may include any number of lumens (illustrated as lumens 38, 40, 42, 58, and 60), which each may hold one or more of a guidewire or optical fiber camera, or may be used for fluid delivery or blood sample extraction. It should be understood that any lumen of system 300 may contain or be fluidly connected to any of the devices (e.g., sensors, guidewire, optical fiber camera) described herein and/or may be used for any of the functions described herein (e.g., fluid delivery, blood sample extraction).

System 300 may include a controller 64, which may be part of any of the control units described herein. Each of the components of system 300 may be operably coupled to the controller 64, and controller 64 may manage operation of electrodes 34 during nerve stimulation, control the gathering of information by various sensors and electrodes 34, and control fluid delivery or extraction for those embodiments with fluid lumens. It should be understood that the various modules described herein may be part of a computing system and are separated in FIG. 3 for explanatory purposes only; it is not necessary for the modules to be physically separate.

Electrodes 34a-34j may be electronically coupled to switching electronics 56, which may be communicably coupled to controller 64. As shown in FIG. 3, a portion of electrodes 34 may be distal electrodes 34a-34d, and a portion of electrodes 34 may be proximal electrodes 34g-34j. Other electrodes 34, such as electrodes 34e and 34f, may be positioned between the proximal and distal electrodes and, depending on the placement of catheter 12, may be used for stimulating either left or right phrenic nerves 26, 28. Hub 36 also may be connected to switching electronics 56 and may be used as an electrode.

Electrodes 34a-34j may be used for both electrically stimulating nerves and for gathering physiological information. When being used for nerve stimulation, a first combination of electrodes (e.g., one, two, three, or more electrodes) may be electrically coupled to a first stimulation module channel 70 for stimulation of a first nerve (e.g., the right phrenic nerve) and a second combination of electrodes (e.g., one, two, three, or more electrodes) may be electrically coupled to a second stimulation module channel 72 for stimulation of a second nerve (e.g., the left phrenic nerve). Electrical signals may be sent from the first and second stimulation module channels 70, 72 to the electrode combinations to cause the electrodes to stimulate the nerves. In other examples, more than two electrode combinations (e.g., 3, 4, or more) may be used to stimulate one or more target nerves, and system 300 may include more than two stimulation module channels.

Electrodes 34a-34f may be further configured to sense physiological information from a patient, such as nerve activity, ECG, or electrical impedance, breathing, etc., as will be described further below. When being used for sensing, one or more of electrodes 34a-34f may be electronically coupled to a signal acquisition module 68. Signal acquisition module 68 may receive signals from electrodes 34.

Switching electronics 56 may selectively couple electrodes 34 to first stimulation module channel 70, second stimulation module channel 72, or signal acquisition module 68. For example, if an electrode 34 (e.g., electrode 34a) is being used to acquire a signal, such as an ECG signal, that electrode 34 may be coupled via switching electronics 56 to signal acquisition module 68. Similarly, if a pair of electrodes (e.g., electrodes 34b and 34d) is being used to stimulate right phrenic nerve 28, those electrodes may be coupled via switching electronics 56 to first stimulation module channel 70. Finally, if a pair of electrodes (e.g., electrodes 34g and 34h) is being used to stimulate left phrenic nerve 26, those electrodes may be coupled via switching electronics 56 to second stimulation module channel 72. Switching electronics 56 may change which electrodes 34 are used for stimulation and which are used for sensing at any given time. In one example, any electrode 34 can be used for nerve stimulation and any electrode 34 can be used for sensing functions described herein. In other words, each electrode 34 may be configured to stimulate nerves, and each electrode 34 may be configured to sense physiological information.

Signal acquisition module 68 may further be coupled to one or more sensors configured to gather physiological information from a patient. For example, system 300 may include one or more of blood gas sensor 62 or pressure sensor 90. These sensors may be located in lumens of catheter 12, outside of the patient in fluid communication with a lumen, on an outer surface of catheter 12, or in any other suitable location. In one example, blood gas sensor 62 may be housed in or fluidly connected to lumen 60, while pressure sensor 90 may be housed in or fluidly connected to lumen 58. Blood gas sensor 62 may measure the amount of $O_2$ or $CO_2$ in the patient's blood. Pressure sensor 90 may measure the central venous pressure (CVP) of the patient. System 300 may additionally or alternatively include other sensors configured to measure other physiological parameters of a patient, such as breath rate, heart rate, ECG, temperature, motion, or air flow.

Signal acquisition module 68 may transmit the signals received from one or more of electrodes 34, blood gas sensor 62, nerve sensor (not shown), and/or pressure sensor 90 to the appropriate processing/filtering module of system 300. For example, signals from pressure sensor 90 may be transmitted to a central venous pressure signal processing/filtering module 84, where the signals are processed and filtered to aid in interpretation of CVP information. Similarly, signals from blood gas sensor 62 may be transmitted to a blood gas signal processing/filtering module 86 for processing and filtering to determine blood gas levels. Signals from electrodes 34, when they are used for sensing, may be sent to nerve signal processing/filtering module 80, ECG signal processing/filtering module 82, or impedance signal processing/filtering module 88, as appropriate. Signals from electrodes 34 or other sensors may be sent to amplification module 78, if necessary, to amplify the signals prior to being sent to the appropriate processing/filtering module.

In one embodiment, sensors can detect information from nerve signals which can be used to help manage the delivery of the therapy for the patient. For example, the electrical activity of a respiratory muscle (e.g., diaphragm) as well as vagal signals from pulmonary stretch receptors, can be used to optimize parameters related to the delivery of the external respiratory support and/or the respiratory muscle stimulation.

For patients with a moderate to high level of consciousness, the electrical activity of the diaphragm can provide an accurate reflection of the patient's neural respiratory drive. In some examples, the electrical activity of the diaphragm may be measured by sensing activities of phrenic nerves. Such measurement may be performed using electrodes in proximity to phrenic nerves or by electromyography. In addition to this neural signal, there are vagally-mediated reflexes which sense lung stretch to limit the volume of inspiration thereby preventing over-distension (Hering-Breuer inflation reflex) and to prevent the de-recruitment of the lung during exhalation (Hering-Breuer deflation reflex).

The positive pressure provided by the external respiratory support, and the negative pressure provided by the stimulated respiratory muscle system can be adjusted and coordinated to respond to these neural signals. For example, increasing the work of breathing provided by electrically-stimulated respiratory muscles (e.g., negative pressure respiration) can allow for a reduction in the positive pressure required from a ventilator. The reduction in positive pressure may reduce the likelihood of barotrauma or lung stretch injury.

Mechanical ventilators often utilize positive end expiratory pressure (PEEP) to hold open portions of the lung at the end of inspiration to protect against decruitment and atelectasis. However, PEEP can increase pulmonary cardiovascular resistance (e.g., affect the cardiac index) and was shown to increase mortality and cause other complications is certain patients (Gavalcanti et al., Effect of Lung Recruitment and Titrated Positive End-Expiratory Pressure (PEEP) vs Low PEEP on Mortality in Patients With Acute Respiratory Distress Syndrome: A Randomized Clinical Trial, JAMA, 2017 Oct. 10; 318(14):1335-1345). To protect against decruitment and atelectasis while avoiding the negative side effects of PEEP, the methods described herein may use a feedback system to precisely time the delivery of negative pressure to the lungs. In one example, sensors may be used to measure signals from a vagus nerve, a phrenic nerve, or other nerves, as well as from a patient monitoring system or external respiratory support device to provide "activity information". The activity information (e.g., nerve activity information) can then be assessed to guide the timing and amplitude of muscle stimulation (e.g., electrical stimulation) throughout the respiratory cycle, i.e. during inspiration and expiration. In one example, to hold open portions of the lung at the end of inspiration, the stimulation can continue to be delivered to the diaphragm or other respiratory muscle, in some examples at a different magnitude, after the completion of the inspiration cycle from the external respiratory support (e.g., mechanical ventilator). The resulting negative end expiratory pressure (NEEP) may mitigate de-recruitment of the lung tissue and prevent atelectasis. In general, in the various therapies described herein, stimulation can be timed to occur during inspiration periods, during expiration periods, during pauses between inspiration/expiration, or during any desired portion of a patient's breath cycle, whether or not the patient is receiving external respiratory support. Devices such as Electrical Impedance Tomography (EIT) utilize electrodes on the patient's chest wall to measure changes in lung volume during ventilation which result in changes of thoracic impedance. EIT can be used to assess respiratory function and guide the application of NEEP, either alone or in combination with external respiratory support.

As non-limiting examples, the electrical activity of the diaphragm can be sensed by one of several devices/methods, such as by electrodes on the catheter 12 (as disclosed in U.S. patent application Ser. No. 15/666,989, filed Aug. 2, 2017, and incorporated by reference herein), by an esophageal probe, or by some other sensor. Separately, vagal electrical signals can be detected by the catheter 12 (as disclosed in U.S. Pat. Pub. No. 20050131485 A1) or by other sensors. The lung contains pulmonary stretch receptors that sense the expansion of the lungs. Overexpansion of the lungs can produce pain signaling which is transmitted via the vagus nerve to the brain. Detection of pain signaling can be an indicator that the magnitude of the pressure from an external respiratory support device (e.g., ventilator) should be reduced. In this situation, the systems and methods described herein may be used to "neurally optimize" breathing assistance to the patient by balancing ventilator support with stimulation to reduce deleterious effects of positive pressure ventilation systems. The combined external respiratory support and stimulation of nerves and/or muscles may provide adequate respiratory support (e.g., gas exchange) and direct respiratory muscle activation/exercise while minimizing the potential for overstretch lung injury and ensuring lower lung recruitment.

In some examples, the systems described herein may include a respiratory muscle stimulator (e.g., catheter 12, electrodes 44, and/or tube 46), a neural sensor (e.g., any electrode described herein, or another sensor configured to sense electrical activity of nerves or muscles), an external respiratory support device (e.g., external respiratory support 88), and a control system (e.g., controller 64, or any of the control units described herein) to manage the delivery of stimulation and ventilation assistance in proportion to and in synchrony with the patient's respiratory efforts and in consideration of pain receptor signaling, based on the measurement of one or more electrical neural signals. The timing and coordination between the external respiratory support device (e.g., ventilator) and muscle stimulator can be synchronized to optimize the support needed by the patient.

Controller 64 may further communicate with display 74, which may serve as a user interface and may have a 2 (see FIG. 1). System 300 may further include software/firmware 76, which may contain the instructions necessary for carrying out the various functions described herein. System 300 also may include data storage 79, for storing information gathered during sensing operations of catheter 12, and/or for storing instructions related to the operation of any of the modules or instructions for carrying out any of the functions described herein. The stimulator, such as catheter 12 or array 13, may contain unique identification features (e.g., RFID), and in the event the systems described herein (e.g., having one or more of controllers/programmers 18, 64) are used to treat multiple patients concurrently, the identification feature may allow the systems to uniquely identify each patient and access that patient's stored patient data.

Once the electrodes (e.g., as part of catheter 12 or array 13) are positioned on or within the patient, various electrodes or electrode combinations can be tested to locate nerves of interest and to determine which electrodes most effectively stimulate the nerves of interest. For example, testing may be done to locate the right phrenic nerve and to determine which group of distal electrodes (e.g., of catheter 12) in the distal electrode assemblies most effectively stimulate the right phrenic nerve. Similarly, testing may be done to locate the left phrenic nerve and to determine which group of proximal electrodes (e.g., of catheter 12) in the proximal electrode assemblies most effectively stimulate the left phrenic nerve. Similarly, testing may be done to locate the intercostal nerve(s) and to determine which group of electrodes (e.g., of the catheter 12, of transcutaneous electrode array 13, or of any other electrode array) most effectively stimulate the intercostal nerve(s).

This testing and nerve location may be controlled and/or monitored via controller 64/control unit 18, which may include testing programming and/or applications. For ease of reference, a "controller" may refer to controller 64, control unit 18, or any other control system/unit described herein. The controller may test the electrodes and electrode combinations to determine which combinations (bipolar, tripolar, quadrupolar, multipolar) of electrodes most effectively stimulate the right phrenic nerve, left phrenic nerve, vagus nerve, and/or intercostal muscles.

As a non-limiting example, testing could involve the use of a signal generator (e.g., signal generator 14 of FIG. 1) to systematically send electrical impulses to selected electrodes. By observing the patient's condition or by using sensors (either within or separate from the catheter), the ideal stimulation electrodes may be identified. Electrodes may serve as both stimulating electrodes and as sensing electrodes, and the medical system may be integrated into a mechanical ventilator, which can be used to sense the patient's condition. Moreover, for example, the controller may be programmed and/or activated to (a) select a first stimulation group of electrodes from the electrode assemblies to stimulate the left phrenic nerve, (b) select a second stimulation group of electrodes from the electrode assemblies to stimulate the right phrenic nerve, (c) select a third stimulation group of electrodes from the electrode assemblies to stimulate the vagus nerve, (d) select a first stimulation current for the first stimulation group of electrodes to stimulate the left phrenic nerve, (e) select a second stimulation current for the second stimulation group of electrodes to stimulate the right phrenic nerve, and (f) select a third stimulation current for the third stimulation group of electrodes to stimulate the vagus nerve. The selection of electrodes and current level may be pre-programmed or input based on the patient's characteristics, or the controller may test different electrode groups and current levels and monitor the patient's response to determine the electrode pairs and current levels.

Alternatively, a transcutaneous noninvasive nerve stimulator device that uses electrical current from a small handheld device to stimulate a nerve for a respiratory muscle can be used to stimulate the target nerve through the skin. Alternatively, one or more other methods can be used to stimulate nerves, for example subcutaneous electrodes or nerve cuffs connected to the controller.

If a greater diaphragm response is desired, electrodes 34 that are closer to the nerve, as determined based on the sensed reaction of the targeted muscle, may be selected for nerve stimulation. In other cases, if less diaphragm response is desired, electrodes 34 that are farther from the nerve, as determined based on sensed muscle reaction, may be selected for nerve stimulation.

In one example, a method for selecting one or more electrodes for nerve stimulation may include inserting intravascular catheter 12 into: a) at least one of left subclavian vein 22 or left jugular vein 32, and b) superior vena cava 24, wherein catheter 12 includes a plurality of electrodes 34, and each electrode 34 of the plurality of electrodes 34 is configured to emit electrical signals to stimulate a nerve; using one or more electrodes 34 of the plurality of electrodes 34 to acquire an electrical signal emitted from the nerve; based on the acquired electrical signal, selecting an electrode 34 or an electrode combination for a nerve stimulation; and using the selected electrode 34 or electrode combination, stimulating the nerve.

Information from blood gas sensor 62 may be used by a health professional, or by controller 64, to adjust stimulation parameters. For example, if blood $O_2$ levels are low (or blood $CO_2$ levels are high) controller 64 may send a signal to electrodes 34 to emit stimulation signals having a higher charge (amplitude×pulse width) or frequency, and may stimulate a sigh breath. Conversely, if blood $O_2$ levels are high (or blood $CO_2$ levels are low), controller 64 may cause electrodes 34 to emit stimulation signals having a lower charge or frequency. Based on information from blood gas sensor 62, the following parameters can be adjusted: stimulation pulse amplitude, stimulation pulse width, stimulation pulse frequency, stimulation duration, and the interval between stimulations/pulse trains (e.g., stimulated breath rate).

For any of the parameter adjustments described herein, increasing stimulation pulse amplitude, width and/or frequency may increase lung volume during a stimulated breath. Increasing stimulation duration may increase lung volume and/or increase the amount of time air remains in the lungs during a stimulated breath, allowing for an extended gas exchange period. Increasing the stimulated breath rate may allow for additional gas exchange periods over a given period of time, which may increase the amount and/or speed of gas exchange.

The systems and catheter 12 described herein may include any combination of sensing features. For example, catheter 12 may be configured to sense ECG, impedance, nerve activity, blood gas levels, and CVP, and the systems may be configured to position catheter 12, select electrodes 34 for stimulation, and select stimulation parameters based on one or more types of information received by sensors or electrodes 34.

Exemplary Methods for Strengthening a Respiratory Muscle

As described previously, the systems and methods described herein may reduce or eliminate the need for a patient to receive external respiratory support (e.g., any device or methods to help correct or otherwise enhance blood gases and or reduce the work of breathing of a patient). As many patients receiving external respiratory support suffer from respiratory muscle atrophy, the systems and methods described herein can be used to build the strength for these muscles over time. As will be described, a relatively small number of stimulation cycles can greatly improve the strength of respiratory muscles until patients no longer need external respiratory support.

In various exemplary methods and systems for stimulating a respiratory muscle of a patient, a stimulator may be positioned adjacent a nerve capable of activating a respiratory muscle. The stimulator may be any stimulation device described herein and may include one or more sets of electrodes for stimulating one or more nerves or muscles.

Maximal inspiratory pressure (MIP or PIMax) is a widely used measure of respiratory muscle strength in patients with suspected respiratory muscle weakness. It is determined by measuring upper airway pressure (mouth for outpatients and trachea for intubated or tracheostomized patients) during a maximal voluntary inspiratory effort. The measured pressure is a composite of the pressure generated by the inspiratory muscles and the elastic recoil pressure of the lungs and chest wall. Often, patients with an absolute MIP value of approximately 30 cm $H_2O$ or less will require some level of external respiratory support. In various examples of this disclosure, stimulation therapy may be administered until the patient's MIP reaches a pre-determined value. In some cases, the pre-determined value may be at least 30 cm $H_2O$. In other cases, the pre-determined value may be at least 35 cm $H_2O$, at least 40 cm $H_2O$, at least 45 cm $H_2O$, or at least 50 cm $H_2O$.

In some therapy methods, external respiratory support initially may be provided for a portion of the patient's breaths during a 24-hour period. In various examples, external respiratory support initially may be provided for at least 20%, 30%, 40%, 50%, 60%, 70%, 80%, 90% or 100% of the patient's breaths in a 24-hour period. Stimulation therapy, as described herein, may be administered while the patient is receiving external respiratory support. Subsequent to administering at least some stimulation therapy, the level of external respiratory support may be reduced, as the patient's respiratory muscle begins strengthening from the stimulation. In one example, at least one of a pressure provided by the external respiratory support or a percentage of breaths assisted by the external respiratory support may be reduced subsequent to administering at least some stimulation therapy. In some examples, the external respiratory support is removed from the patient after administering at least some stimulation therapy. Stimulation therapy may be continued after removal of the external respiratory support (e.g., for at least 1 day, for at least 2 days, for at least 3 days, etc.). In some examples, a drug may be delivered to the patient prior to, during, or after stimulation therapy.

Figure 4:
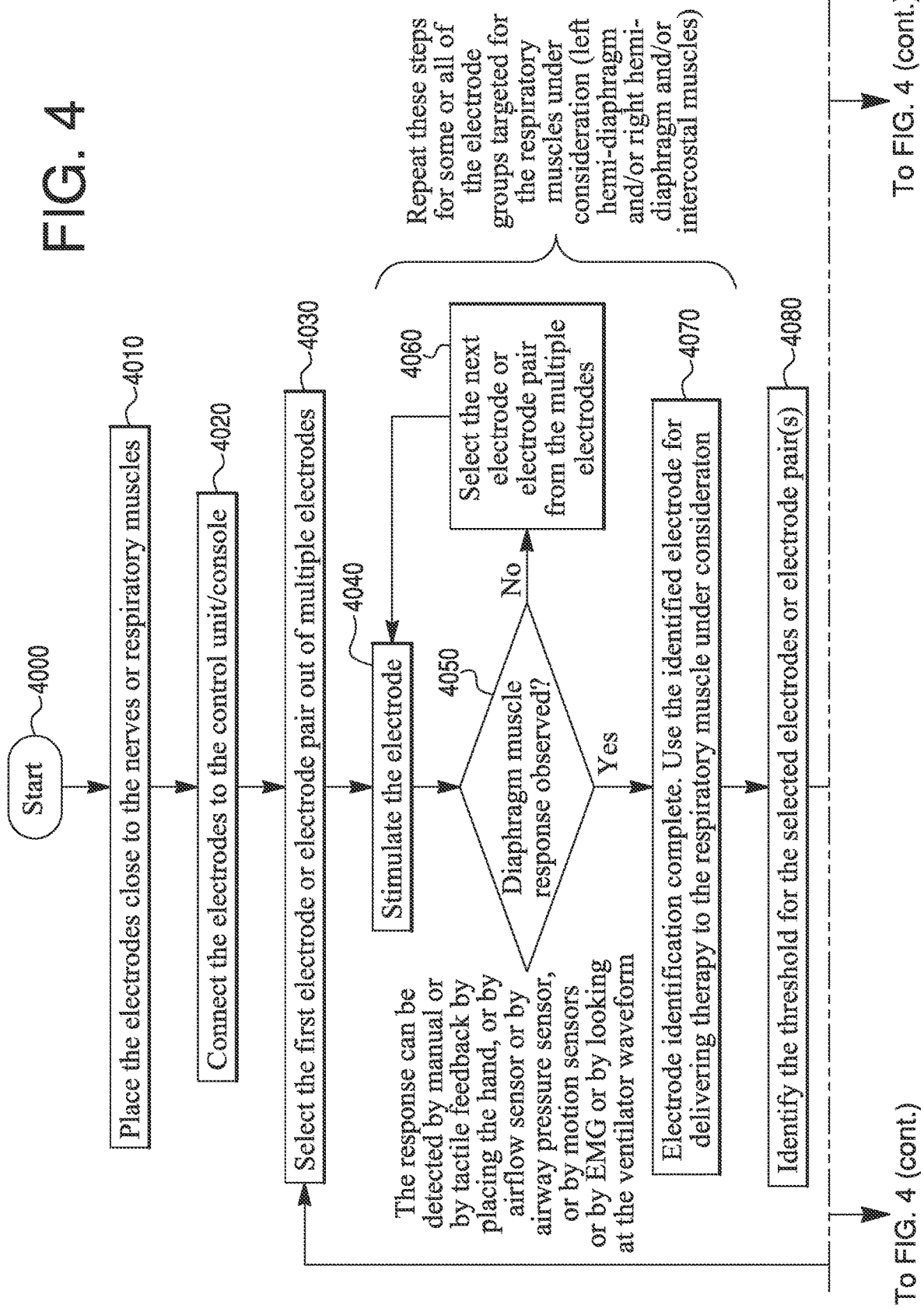
FIG. 4 illustrates a flowchart describing an exemplary therapy for increasing the strength of a respiratory muscle.
Figure 4:
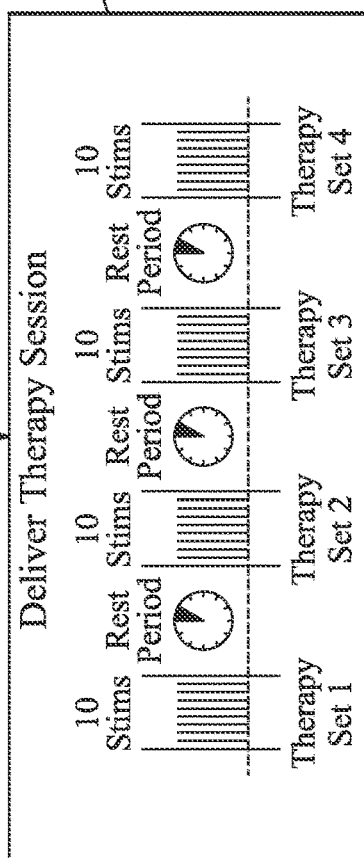
Figure 4:
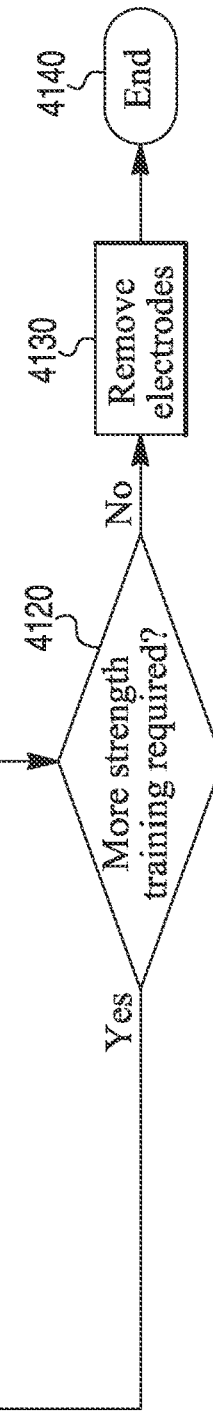

The flowchart of FIG. 4 describes a therapy method according to an exemplary embodiment. An exemplary method for providing therapy may start at step 4000. In step 4010, a stimulator having electrodes, for example catheter 12 or a transdermal stimulator, may be positioned adjacent a nerve that activates a respiratory muscle or a nerve in proximity to the respiratory muscles, and in step 4020, the electrodes may be connected to a control unit. In some examples, the stimulator may include multiple sets of electrodes, such as intravascular electrodes and transdermal electrodes, or esophageal electrodes and transdermal electrodes. The electrodes of the stimulator may be used to stimulate one or more respiratory muscles at time. For example, a first set may be used to stimulate a first respiratory muscle, and a second set may be used to stimulate a second respiratory muscle. In other examples, both sets of electrodes may be used to stimulate the same respiratory muscle. The first and second respiratory muscles may be the diaphragm, the intercostal muscles, or any other muscle that affects breathing. Steps 4010 and 4020 can be done in any order.

Steps 4030-4070 illustrate a mapping (e.g., electrode identification) process that may be used to select one or more electrodes for delivering therapy to one or more respiratory muscles. The mapping process may be carried out by an operator, who may select various electrodes or electrode combinations for testing, or automatically by a pre-programmed controller. Furthermore, either an operator or an automated system may determine stimulation thresholds, select electrodes for stimulation therapy, and/or determine the ideal stimulation levels for therapy.

In step 4030, a first electrode or electrode combination (e.g., an electrode pair) may be selected for testing to determine whether the selected electrode/electrodes are suitable for therapy. Referring to step 4040, the electrode or combination of electrodes may be activated/stimulated to emit an electrical signal. The electrical signal may stimulate a nerve or muscle, which may cause a contraction of a respiratory muscle. In the example of FIG. 4, in step 4050 a determination is made about whether a diaphragm muscle response is observed. If so, the identified electrode or electrodes can be used to deliver therapy to the respiratory muscle (e.g., the diaphragm) under consideration (step 4070). If no diaphragm response is observed, the next electrode or electrode combination may be selected (step 4060) and tested as previously described in connection with steps 4040 and 4050.

The contraction of the respiratory muscle can be detected visually or via tactile feedback by an operator. Sensors such as a breath sensor, airflow sensor, motion sensor, EMG detector, etc. also or alternatively may be used to confirm that the stimulator is effectively activating the targeted respiratory muscle at the desired level. Data from a patient monitor, such as the pressure waveform on a mechanical ventilator, can be used to assess the level of muscle stimulation/contraction. Upon sensing the contraction of the respiratory muscle, the selection of the electrodes and/or the stimulation levels can be adjusted, by an operator or automatically by controller 64, to the desired level to provide the appropriate therapy. In one example, at least one stimulation parameter is adjusted to achieve a desired contraction of the respiratory muscle. Steps 4040-4070 can be repeated for each of multiple electrode sets to identify electrodes for delivering therapy to each respiratory muscle under consideration (e.g., left hemi-diaphragm, right hemi-diaphragm, and/or intercostal muscles).

In step 4080, the threshold for each selected electrode or electrode combination is identified. The threshold may be the level of one or more parameters (e.g., charge, amplitude, frequency, or pulse width) of stimulation necessary to elicit a muscle response. The stimulation threshold may be determined by palpating the respiratory muscle of the patient, as shown by the illustration of a hand in FIG. 1. In other examples, the stimulation threshold may be determined by observing at least one of a pressure or a volume data from an external respiratory support system. In certain examples, the stimulation threshold may be determined by central venous pressure. In some examples, the stimulation threshold may be measured using a device, such as, for example, accelerometers or impedance sensors. In step 4090, the stimulation parameters for each selected electrode or electrode combination may be determined. Stimulation parameters may include amplitude, frequency, stimulation rate, stimulation hold, or any other parameters mentioned in this disclosure.

In step 4100, therapy may be delivered to strengthen one or more respiratory muscles. Stimulations of the nerves/muscles may be initiated by an operator, automatically by a controller, or by the patient. For example, the patient may initiate the therapy session or may initiate one or more breaths (e.g., respiratory muscle contractions) of the therapy session. In one example, the therapy may include four therapy sets, each including 10 stimulations, with a rest period between each therapy set. Other specific therapies are described in more detail below and may be delivered in step 4100. In step 4110, the patient may rest prior to the next therapy session. In other words, electrical stimulation may be discontinued for a period of time until the next therapy session. In some examples, the rest period may be 1-3 hours. In other examples, the rest period may be 24-48 hours. In still other examples, the rest period may be 3-5 hours, 5-7 hours, 8-24 hours, or greater than 48 hours.

In step 4120, a determination may be made about whether more strength training is required or desired for the respiratory muscle. In some examples, additional therapy sessions may be performed until external respiratory support can be removed from the patient. If additional therapy is required, the process may begin again at step 4030, and electrodes may be selected and then used to deliver therapy to one or more respiratory muscles. If no additional therapy is required, the electrodes may be removed from the patient (step 4130). In step 4140, the method in which therapy was provided may be ended.

Referring back to steps 4090 and 4100, either before or during a therapy session, an operator or an automated controller can select and adjust one or more of the below inputs. In some cases, one or more parameters may be adjusted between consecutive stimulations of a therapy session.

Stimulation Amplitude: the amount of energy being delivered to the nerve as characterized by the amplitude of current or voltage on the electrode(s).

Stimulation Pulse Width or Stimulation Pulse length: the time over which an electrical stimulation pulse is delivered generally ranging from 10 micro seconds to 1200 micro seconds, or between 100 and 300 micro seconds.

Stimulation Rate: the rate at which the stimulation trains (series of stimulation pulses) are delivered. In some examples, the stimulation rate may be adjusted during stimulation therapy. In one example, a first time period between a first pair of consecutive stimulations is different than a second time period between a second pair of consecutive stimulations.

Stimulation Frequency: the frequency of delivering stimulation pulses in a stimulation train. In various examples, the stimulation frequency range is between 1 Hz to 50 Hz, between 10 Hz and 40 Hz, or between 11 Hz and 25 Hz.

Stimulation Hold: the period of time that a muscle or muscle fibers are held in the contracted state by extending the length/duration of the stimulation pulse train in order to further exercise the targeted muscle.

Stimulation to Stimulation Rest: the rest period time between consecutive stimulated diaphragm contractions in either a therapy set or therapy session, in one example ranging from 0.5 seconds to 120 seconds. The stimulation to stimulation rest may range from 0.5 to 4 seconds, in the event that stimulation is provided with each patient breath for a period of time. Or as an alternative example, the stimulation to stimulation rest period can be up to 30 seconds or longer when allowing the patient's muscle to rest or allowing the patient to receive external respiratory support between each stimulation, or stimulated breath.

Therapy Session: In one example, a therapy session may include a number of stimulated diaphragm contractions that are provided to a patient in a relatively short period of time (e.g. approximately 1 hour or less).

Stimulations per Therapy Session: The number of stimulation pulse trains, resulting in distinct muscle contractions, typically ranging from 1 to 150, or more specifically from 10 to 50, during a therapy session.

Stimulation Sets: In some cases a therapy session may be divided into therapy sets. For example, if 40 breaths are to be stimulated in one therapy session, those 40 breaths could be stimulated in four therapy sets of 10 breaths with a brief period (e.g., 30 seconds to 5 minutes) of rest (e.g., Set to Set Rest) between sets.

Stimulations per Set: The number of stimulations delivered in a set; may range from 5 to 100, or more specifically from 5 to 20 stimulations per set.

Session to Session Rest period: time between therapy sessions, may be 1 hour or longer, 2 hours or more, or 3 hours or more. In the example where one session is provided each day, the rest period may be approximately 24 hours. If therapy sessions are skipped for medical/other reasons or, for example, over the weekend, the Session to Session Rest period may be two to three days.

Therapy sessions per day: the number of therapy sessions per day may be between 1 and 3 sessions, with each session including between 10 and 150 stimulations. For relatively short therapy sessions, such as for those lasting approximately 5 minutes or less, it may be desirable in some circumstances for certain patients to receive 1 or 2 therapy sessions each hour for several hours per day. In some situations, therapy sessions may be limited to daytime hours to allow patients an opportunity to recover overnight.

Degree of external respiratory support: the operator can determine the level and type of external respiratory support that will be provided during various portions of a therapy session. The degree of external respiratory support may depend on the condition of the patient, his/her ability to independently move enough air to provide adequate gas exchange, the amount of respiratory support provided by the stimulation, and the level of consciousness of the patient.

Weekly frequency: In some examples, the patient may receive stimulation therapy 4 to 7 days per week until they are no longer dependent on external respiratory support.

In one embodiment, an operator may engage the system through an operator interface and select a desired number of stimulation pulse trains (stimulations) to deliver to the target nerve or muscle either for a therapy set or for a therapy session, typically ranging from 1 to 150 stimulations. Alternatively, the number of stimulations can be greater if desired. The operator can select the duration of each stimulation and the time between the deliveries of each stimulation, the stimulation period. In one example, the pulse width for each pulse in the stimulations may be between 50 and 300 micro seconds, but could alternatively be outside this range. The stimulation to stimulation rest period, the time between consecutive stimulations in a set or therapy session, may be between 0.5 and 60 seconds. In some examples, the operator can also select the amplitude and profile of the stimulation pulses including various ramp shapes and other characteristics. Profiles may vary depending on the way in which the stimulation energy is being delivered to the nerve, the location from the array to the nerve, the type of muscle being stimulated, and the level of stimulation desired for each patient at that phase of their therapy.

In one exemplary therapy session, catheter 12 may be positioned in the vasculature to extend adjacent or across the left and right phrenic nerves 26, 28. Appropriate distal and proximal electrode pairs may be selected to cause a therapeutic contraction of the respiratory muscle, in this case both the left and right hem i-diaphragm muscles. The operator may set the stimulation pulse train length at 1.2 seconds and pulse amplitude which is 100% of the threshold value and the initial pulse width which is 100% of the threshold value. The pulse width can be modulated between stimulation pulses in the stimulation pulse train. In some cases, the pulse amplitude can be modulated between stimulation pulses in the stimulation pulse train. Using the remote hand held controller 20, the operator may provide a therapy set of 10 stimulation pulse trains. In some examples, each of the stimulation pulse trains may be timed to coincide with a breath delivered by a mechanical ventilator or the patient's spontaneous breath.

In some embodiments, the therapy system can communicate directly with a mechanical ventilator, or other external respiratory support system (e.g., external respiratory support 88), to coordinate the therapy delivery with the support provided by the external device. As previously described, sensors detecting activity from diaphragm muscles, nerves (e.g. phrenic nerves, vagus nerves, etc.) or other patient monitors or respiratory support devices can be used to trigger stimulation and/or breath delivery from a mechanical ventilator. Also, as a non-limiting example, the systems described herein may be operably connected (e.g., hardwired, wireless, etc.) to receive a signal from the mechanical ventilator indicating the initiation of a breath to the patient, and the systems can synchronize the delivery of the stimulation pulse train to coordinate with a desired phase of the breath. In another example, an operator may set the stimulation parameters and ask the patient to activate their breathing muscles. The operator may then coordinate the trigger of electrical stimulation with the patient efforts to provide maximum exercise of the muscles. In another example, external respiratory support 88 can be reduced or even eliminated during a portion of or all of the delivery of a stimulation set or stimulation session.

In the example in which 10 stimulations pulse trains are provided, they can be timed to 10 sequential breaths, or the operator may skip one or more breaths to allow the patient to rest periodically between stimulations. After the 10 stimulation pulse trains are delivered, the patient may be allowed to rest for a period of time, for example 30 seconds to 5 minutes. After a suitable rest, the operator can initiate a second set, for example 10 breaths, again followed by a resting period. The operator can deliver several sets, in this example 4 sets, that each include 10 stimulations. Each stimulation may cause a muscle contraction, for a total of 40 muscle contractions over a 1 to 15-minute period. Of course, the desired number of stimulations for a session could be delivered in a single set, if desired. The patient may then be permitted to rest for 1 or more hours, and in some cases at least 3 hours, and potentially as long as 24 or 48 hours before beginning another therapy session. In some instances, two to three, or more, therapy sessions are delivered each day. Regardless, the number of stimulations provided to the respiratory muscles may be a small fraction of the breaths required by the patient each day. In the previously-described example of 40 stimulations/day, the number of stimulations delivered is approximately less than 0.2% of the breaths taken by or delivered to the patient per day.

In one example, the stimulation parameters may be kept the same from one stimulation that causes muscle contraction to the next stimulation, from one therapy set to the next therapy set, from one session to the next session, or from one day to the next day. In other examples, one of the parameters, such as the stimulation amplitude, the stimulation frequency, the stimulation hold time, or the resistance of the breathing circuit, may be increased or decreased between two stimulations that cause muscle contractions, between two sets, between two sessions, or between two days. The factors to consider while changing parameters may be patient tolerance, unintended stimulation of other structures, fatigue, or a desire for increased strength.

Figure 5:
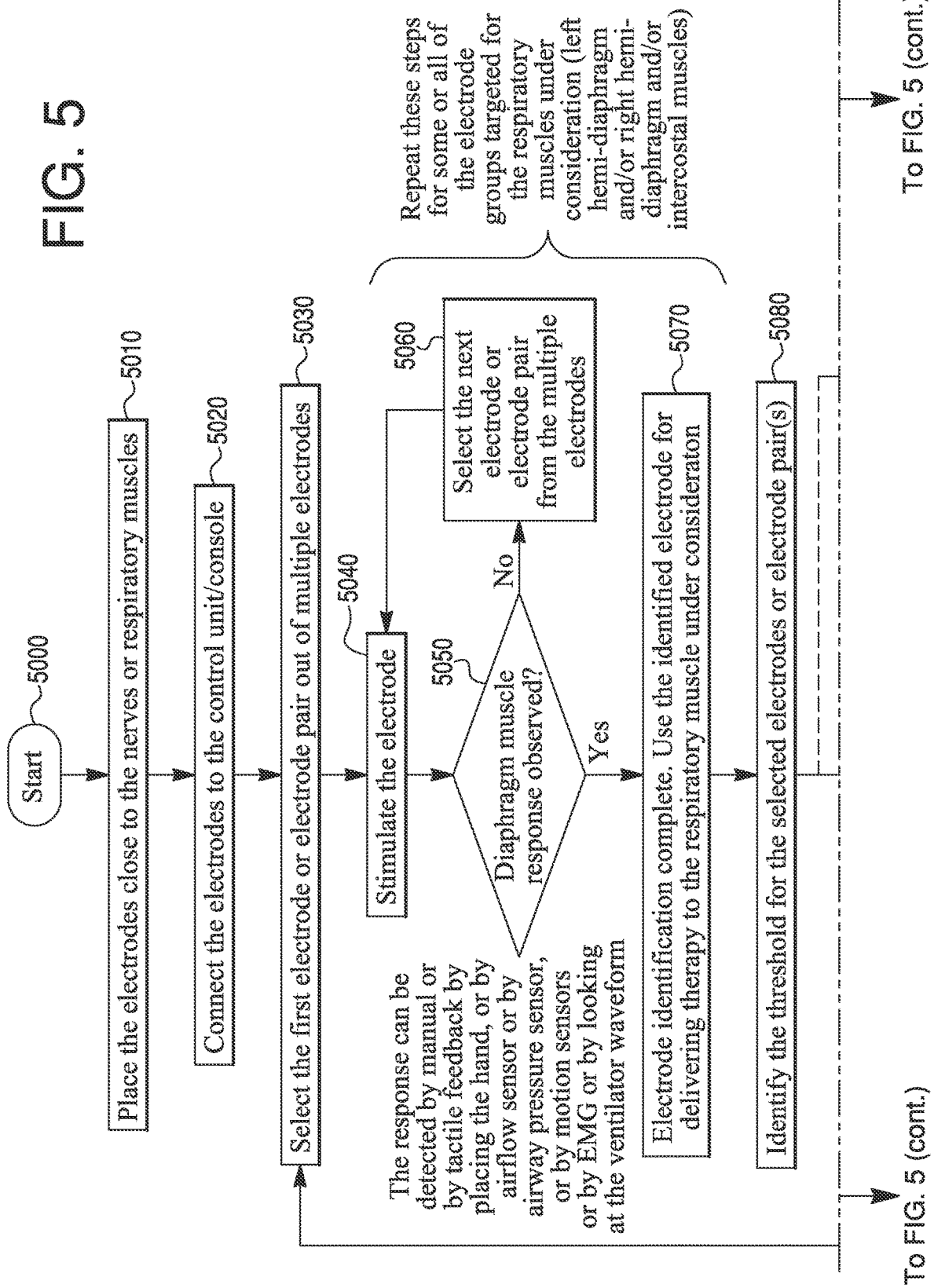
FIG. 5 illustrates a flowchart describing an alternate exemplary therapy for increasing the endurance of a respiratory muscle.
Figure 5:
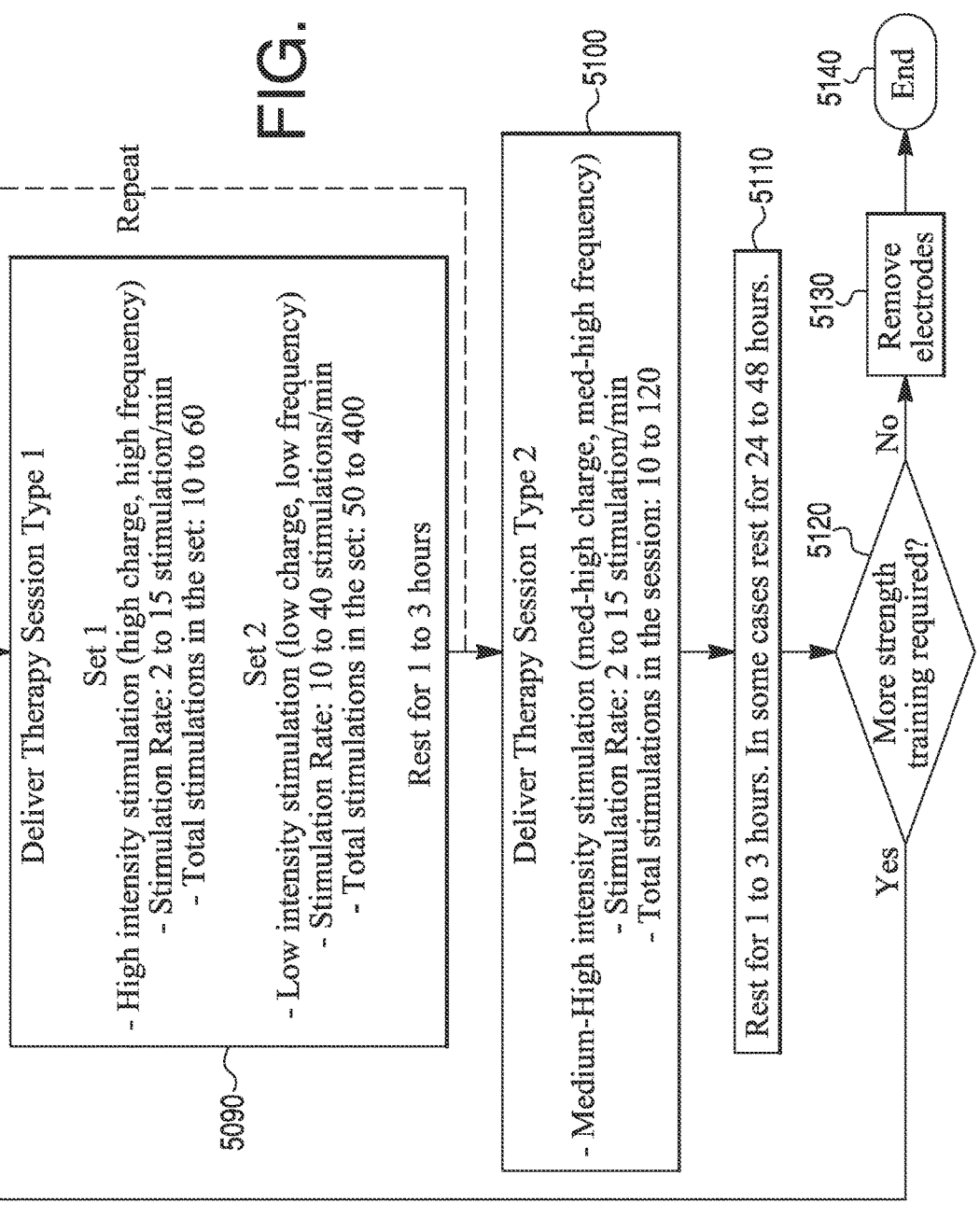

The flowchart of FIG. 5 describes a therapy method, according to another exemplary embodiment, to increase the endurance of the respiratory muscles. Steps 5000-5080 are analogous to steps 4000-4080 of FIG. 4 and therefore are not described again here. Referring to steps 5090 and 5100, two or three sessions of therapy may be delivered in a day. The therapy may be repeated every day. Alternatively, there may be a break between two therapy days of 1 to 3 days or more days.

Referring to step 5090, the first session of the day may include a first set, in which 10 to 60 high amplitude stimulation trains (e.g., stimulation with pulses in a train that have charges from 150% to 300% of a threshold value or frequencies from 20 Hz to 40 Hz) that contract the muscles are delivered at a low stimulation rate (e.g., 2 to 15 stimulations per minute) for 1 to 5 minutes, or for 1 to 3 minutes, followed by a short rest period of 60 seconds to 3 minutes. A second set of the first session may include low amplitude stimulation (e.g., stimulation with pulses in a train that have charges close to a threshold value or frequencies from 8 Hz to 15 Hz) at a high stimulation rate (e.g., between 10-40 stimulations per minute) for 5 to 10 minutes. The second session of the day may be exactly the same as the first session, or some of the stimulation parameters can be adjusted. Referring to step 5100, the third session may include delivering medium-high amplitude stimulations (e.g., stimulation with pulses in a train that have charges from 100% to 150% of a threshold value or frequencies from 15 Hz to 20 Hz) at a low stimulation rate (e.g., 2 to 12 stimulations per minute) for 5 to 10 minutes. The patient may be permitted to rest for 1 or more hours, in some cases at least 3 hours, and potentially as long as 24 to 48 hours between two therapy sessions. Steps 5120-5140 are analogous to steps 4120-4140 of FIG. 4 and therefore are not described again here.

FIG. 6. illustrates clinical data related to the improvement in maximum inspiratory pressure (MIP) of two patients over a period of time. Each of the two patients initially received stimulation therapy having the same stimulation parameters, which are shown in the "Exemplary Parameter Value" column of the below chart. Patient 1 received therapy sessions for most days during a 3-week period and the absolute MIP level increased approximately 12 cm $H_2O$ every 7 days, or 1.7 cm $H_2O$ per day. Patient 2 received therapy over 6 days, during which the patient's absolute MIP increased from 10 cm $H_2O$ to 24 cm $H_2O$, a rate of increase of 2.33 cm $H_2O$ per day, after which the therapy was discontinued and the MIP stayed essentially constant between 23 and 32 cm $H_2O$, showing little or slow improvement over the following two weeks while the patient continued to receive external respiratory support. Patient 1 was able to breathe independent of external respiratory support once achieving an MIP value of approximately 40 cm $H_2O$.

Referring back to step 4090 or to any other therapy session described herein, exemplary parameters for therapy sessions may fall within certain ranges. In the chart below, the first column titled "therapy parameter" lists various characteristics of a therapy session. The second column titled "exemplary parameter value" includes an exemplary number or time period corresponding to the listed therapy parameters. The remaining two columns list exemplary low and high ends of a range for the listed therapy parameters. In one example, a therapy session may include settings corresponding to the "exemplary parameter value" column. However, in other examples, a therapy session may include settings for each therapy parameter between the ranges described by the low and high end columns. In yet other examples, a therapy session may have parameters that mostly fall within the ranges listed in the below chart, but certain parameters may fall outside of the listed ranges.

| Therapy Parameter | Exemplary Parameter Value | Exemplary Low-End of Parameter Range | Exemplary High End of Parameter Range |
| --- | --- | --- | --- |
| Stimulations/Set | 10 | 5 | 100 |
| Stimulations/Therapy Session | 40 | 5 | 150 |
| Sets/Session | 4 | 1 | 10 |
| Therapy Sessions/Day | 3 | 1 | 48 |
| Stim to Stim Rest | 1 sec | 0.5 sec | 120 sec |
| Set to Set Rest | 30 sec-5 min | 15 sec | 30 min |
| Session to Session Rest | 3 hrs | 1 hr | 24 hrs |
| % of breaths stimulated | 0.14% | 0.10% | 20.00% |

In another example of a therapy session, up to 100 stimulations may be delivered during a first set of a therapy session to enable the respiratory muscle to contract up to 100 times. The stimulation may be paused for at least 30 seconds, and in some cases one or more minutes, after which a second set of up to 100 stimulations may be delivered. Then the stimulation may be paused for a session to session rest period of 1 or more hours until a second therapy session is delivered. In the next session, the stimulator may be activated again to cause the respiratory muscle to contract up to 100 times. The activations and ceasing of activations for any therapy described herein may be repeated one or more times.

Furthermore, any stimulation therapy or combinations of external respiration support and stimulation therapy may be repeated for a set number of hours or days, such as for 24 hours or for 48 hours.

In any example described herein, the stimulator may include multiple sets of electrodes. A first set of electrodes may be used to deliver therapy to a first nerve or directly to a respiratory muscle, and a second set of electrodes may be used to deliver the same therapy (e.g., the same stimulation patterns) to either the same or different nerve to activate the same or different muscle, or directly to a different muscle.

In another example of a therapy session, stimulation signals may be delivered over a total period of time of approximately 2 hours or less, during one or more therapy sessions during that total of 2 hours or less, during a 24-hour period. In another example, stimulation signals may be delivered over a total period of time of 5 hours or less during a 24-hour period.

In other examples of therapy sessions, stimulation signals may be delivered to contract one or more respiratory muscles for no more than: 20% of the breaths taken by or delivered to the patient in a 24-hour period; 10% of the breaths taken by or delivered to the patient in a 24-hour period; 2% of the breaths taken by or delivered to the patient in a 24-hour period; or 0.2% of the breaths taken by or delivered to the patient in a 24-hour period.

In another example, a brief stimulation therapy session lasting approximately 3 to 10 minutes may be delivered 12 to 24 times over a 24-hour period; 6 to 12 times over a 24 hour period; or once in a 24 hour period.

In another example, therapy sessions may be administered until the patient no longer requires external respiratory support; or up to 48 hours after the time at which the patient no longer requires, or is no longer receiving, external respiratory support.

Various examples of the subject disclosure may be implemented soon after the patient begins using external respiratory support (e.g., mechanical ventilation) to help reduce the loss of strength and or endurance of a respiratory muscle. Various examples of this disclosure can be used to help reduce the level of injury to a patient's lungs, heart, brain and/or other organs of the body.

The systems described herein can be programmed to vary the profile of the stimulation pulse trains from time to time. For example, every tenth stimulation pulse train can be programmed to be longer than the others to produce a deeper or longer breath (e.g., sigh breath). In this case the duration of the stimulation pulse train between two adjacent pulse trains will vary.

In some examples, therapy may be continued and steps related to activating the stimulator and ceasing activation of the stimulator may be repeated until MIP reaches a predetermined value.

Furthermore, steps of any therapy treatment described herein may be carried out with respect to more than one nerve and more than one respiratory muscle. Stimulations of multiple nerves (and one or more respiratory muscles) may be synchronized so that the patient's muscle or muscles are stimulated at the same time. To achieve this synchronization, two or more combinations of selected electrodes may be activated at the same time during a therapy session. For example, if the first set of electrodes emits electrical signals up to 100 times, the second set of electrodes may emit electrical up to 100 times, with each emission of the second set corresponding to an emission of the first set of electrodes. In one example, the first and second sets of electrodes may be used to stimulate the left and right phrenic nerves to cause synchronized contractions of the left and right hem i-diaphragm. In another example, the first set may be used to stimulate the diaphragm, and the second set may be used to stimulate the intercostal muscles. Both stimulations may occur at the same time in the patient breath cycle. In yet another example, the patient's nerves/muscles may be stimulated during an inspiratory period of the patient's ventilator or other external respiratory support.

While most examples described herein consider that a therapy session will be delivered by a health care professional, other approaches of therapy delivery may be utilized that also deliver infrequent respiratory muscle stimulation to build strength. As a non-limiting example, a closed-loop automated example of the system of this disclosure can be designed to deliver a stimulation to a respiratory muscle at a specific duty cycle such as 1 stimulation for every X breaths, where X could range from 10 to 1000 when building strength for a respiratory muscle. This approach may provide for periodic muscle stimulation with a predetermined number of resting breaths in between. X may be as small as 2 and as large as 10,000 in various examples. When using the systems and methods described herein to prevent respiratory muscle atrophy as well as lung and brain injury, the stimulations can be provided more frequently, potentially as often as every breath.

Various electrodes may be used to stimulate nerves and/or muscles as described in this disclosure. As examples, the stimulators described herein may include one or more of: nerve stimulation electrodes, endotracheal electrodes, endoesophageal electrodes, intravascular electrodes, transcutaneous electrodes, intracutaneous electrodes, electromagnetic beam electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, or probe electrodes. Furthermore, the stimulation energy may be delivered by an energy form that includes at least one of mechanical, electrical, ultrasonic, photonic, or electromagnetic energy.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method of stimulating a respiratory muscle, the method comprising:
delivering a first set of stimulation trains, wherein each stimulation train of the first set of stimulation trains causes the respiratory muscle to contract and includes pulses delivered at a first frequency;

delivering a second set of stimulation trains, wherein each stimulation train of the second set of stimulation trains causes the respiratory muscle to contract and includes pulses delivered at a second frequency; and delivering a third set of stimulation trains, wherein each stimulation train of the third set of stimulation trains causes the respiratory muscle to contract and includes pulses delivered at a third frequency;

wherein the third frequency is less than the first frequency, and greater than the second frequency.

2. The method of claim 1, wherein the first frequency, the second frequency, and the third frequency are each 8-40 Hz.

3. The method of claim 1, wherein the first set of stimulation trains has a duration of 1-3 minutes, and wherein the second set of stimulation trains and the third set of stimulation trains each has a duration of 5 to 10 minutes.

4. The method of claim 1, further comprising, delivering no stimulation trains during a 1-3 minute period between the first set of stimulation trains and the second set of stimulation trains.

5. The method of claim 1, further comprising, after delivering the second set of stimulation trains, and prior to delivering the third set of stimulation trains:

delivering a fourth set of stimulation trains, wherein each stimulation train of the fourth set of stimulation trains causes the respiratory muscle to contract and includes pulses delivered at the first frequency; and delivering a fifth set of stimulation trains, wherein each stimulation train of the fifth set of stimulation trains causes the respiratory muscle to contract and includes pulses delivered at the second frequency.

6. The method of claim 5, further comprising, delivering no stimulation trains during a 1-3 hour period between the second set of stimulation trains and the fourth set of stimulation trains.

7. The method of claim 6, further comprising:

delivering no stimulation trains during a 1-3 minute period between the fourth set of stimulation trains and the fifth set of stimulation trains; and delivering no stimulation trains during a 1-3 hour period between the fifth set of stimulation trains and the third set of stimulation trains.

8. The method of claim 1, wherein the method increases the endurance of the respiratory muscle.

9. The method of claim 1, further comprising identifying a threshold value;

wherein the first set of stimulation trains is delivered at a rate of 2-15 trains per minute, and each stimulation train of the first set of stimulation trains includes pulses delivered at a charge that is 150%-300% of the threshold value;

wherein the second set of stimulation trains is delivered at a rate of 10-40 trains per minute, and each stimulation train of the second set of stimulation trains includes pulses delivered at a charge that is about 100% of the threshold value; and wherein the third set of stimulation trains is delivered at a rate of 2-12 trains per minute, and each stimulation train of the third set of stimulation trains includes pulses delivered at a charge that is 100%-150% of the threshold value.

10. A method of stimulating a respiratory muscle, the method comprising:

positioning a stimulator inside a patient and adjacent to a nerve capable of activating the respiratory muscle;

delivering a first set of stimulation trains to the nerve via the stimulator, wherein each stimulation train of the first set of stimulation trains causes the respiratory muscle to contract and includes pulses delivered at a frequency of 20-40 Hz;

delivering a second set of stimulation trains to the nerve via the stimulator, wherein each stimulation train of the second set of stimulation trains causes the respiratory muscle to contract and includes pulses delivered at a frequency of 8-15 Hz; and delivering a third set of stimulation trains to the nerve via the stimulator, wherein each stimulation train of the third set of stimulation trains causes the respiratory muscle to contract and includes pulses delivered at a frequency of 15-20 Hz.

11. The method of claim 10, wherein the first set of stimulation trains includes 10-60 stimulation trains, the second set of stimulation trains includes 50-400 stimulation trains, and the third set of stimulation trains includes 10-120 stimulation trains.

12. The method of claim 11, wherein the first set of stimulation trains is delivered at a rate of 2-15 trains per minute, the second set of stimulation trains is delivered at a rate of 10-40 trains per minute; and the third set of stimulation trains is delivered at a rate of 2-12 trains per minute.

13. The method of claim 12, wherein the first set of stimulation trains has a duration of 1-3 minutes, the second set of stimulation trains has a duration of 5-10 minutes, and the third set of stimulation trains has a duration of 5-10 minutes.

14. The method of claim 13, wherein the method further comprises:

delivering no stimulation trains during a 1-3 minute period between the first set of stimulation trains and the second set of stimulation trains; and delivering no stimulation trains during a 1-3 hour period between the second set of stimulation trains and the third set of stimulation trains.

15. The method of claim 10, further comprising:

after delivering the third set of stimulation trains, determining that additional stimulation is required to increase the endurance of the respiratory muscle; and after the determining step:

delivering a fourth set of stimulation trains to the nerve via the stimulator, wherein each stimulation train of the fourth set of stimulation trains causes the respiratory muscle to contract and includes pulses delivered at a frequency of 20-40 Hz;

delivering a fifth set of stimulation trains to the nerve via the stimulator, wherein each stimulation train of the fifth set of stimulation trains causes the respiratory muscle to contract and includes pulses delivered at a frequency of 8-15 Hz; and delivering a sixth set of stimulation trains to the nerve via the stimulator, wherein each stimulation train of the sixth set of stimulation trains causes the respiratory muscle to contract and includes pulses delivered at a frequency of 15-20 Hz.

16. The method of claim 15, wherein the fourth set of stimulation trains is delivered at a rate of 2-15 trains per minute, the fifth set of stimulation trains is delivered at a rate of 10-40 trains per minute; and the sixth set of stimulation trains is delivered at a rate of 2-12 trains per minute.

17. The method of claim 16, wherein the first set of stimulation trains includes 10-60 stimulation trains, the second set of stimulation trains includes 50-400 stimulation trains, the third set of stimulation trains includes 10-120 stimulation trains, the fourth set of stimulation trains includes 10-60 stimulation trains, the fifth set of stimulation trains includes 50-400 stimulation trains, and the sixth set of stimulation trains includes 10-120 stimulation trains.

18. The method of claim 16, further comprising delivering no stimulation trains during a 24-48 hour period between the third set of stimulation trains and the fourth set of stimulation trains.

19. The method of claim 18, further comprising:
delivering no stimulation trains during a 1-3 minute period between the first set of stimulation trains and the second set of stimulation trains;
delivering no stimulation trains during a 1-3 hour period between the second set of stimulation trains and the third set of stimulation trains;
delivering no stimulation trains during a 24-48 hour period between the third set of stimulation trains and the fourth set of stimulation trains;
delivering no stimulation trains during a 1-3 minute period between the fourth set of stimulation trains and the fifth set of stimulation trains; and
delivering no stimulation trains during a 1-3 hour period between the fifth set of stimulation trains and the sixth set of stimulation trains.

20. A method of stimulating a respiratory muscle, the method comprising:
identify a threshold value for a charge required to stimulate a respiratory muscle;
after identifying the threshold value, delivering a first set of stimulation trains at a rate of 2-15 trains per minute, wherein each stimulation train of the first set of stimulation trains includes pulses delivered at a charge that is 150%-300% of the threshold value;
after delivering the first set of stimulation trains, delivering a second set of stimulation trains at a rate of 10-40 trains per minute, wherein each stimulation train of the second set of stimulation trains includes pulses delivered at a charge that is about 100% of the threshold value; and
after delivering the second set of stimulation trains, delivering a third set of stimulation trains at a rate of 2-12 trains per minute, wherein each stimulation train of the third set of stimulation trains includes pulses delivered at a charge that is 100%-150% of the threshold value.

21. The method of claim 20, wherein the threshold value is a threshold value for an electrode or an electrode combination, and the method further comprises, prior to identifying the threshold value, positioning the electrode or electrode combination in a blood vessel.

22. The method of claim 21, further comprising:
removing the electrode or electrode combination from the blood vessel; and
after the third set of stimulation trains is delivered, and prior to removing the electrode or electrode combination from the blood vessel:
determining that additional stimulation is required to increase the endurance of the respiratory muscle; and
delivering a fourth set of stimulation trains, wherein each stimulation train of the fourth set of stimulation trains includes pulses delivered at a charge that is 150%-300% of the threshold value.

* * * * *